(12) United States Patent
Johnson et al.

(10) Patent No.: US 11,155,527 B2
(45) Date of Patent: Oct. 26, 2021

(54) MACROMOLECULES COMPRISING TRIAZOLES AND RELATED COMPOUNDS

(71) Applicant: Massachusetts Institute of Technology, Cambridge, MA (US)

(72) Inventors: Jeremiah A. Johnson, Boston, MA (US); Yoshiki Shibuya, Kanagawa (JP); Hung Vanthanh Nguyen, Cambridge, MA (US); Yivan Jiang, Revere, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 112 days.

(21) Appl. No.: 16/592,199

(22) Filed: Oct. 3, 2019

(65) Prior Publication Data

US 2020/0115351 A1    Apr. 16, 2020

Related U.S. Application Data

(60) Provisional application No. 62/740,492, filed on Oct. 3, 2018.

(51) Int. Cl.
| | | |
|---|---|---|
| *C07D 271/04* | (2006.01) | |
| *C08G 61/12* | (2006.01) | |
| *C07C 43/14* | (2006.01) | |
| *C07C 247/08* | (2006.01) | |

(52) U.S. Cl.
CPC ............ *C07D 271/04* (2013.01); *C07C 43/14* (2013.01); *C07C 247/08* (2013.01); *C08G 61/123* (2013.01); *C08G 2261/3228* (2013.01); *C08G 2261/334* (2013.01)

(58) Field of Classification Search
CPC ..... C07D 271/04; C07C 43/14; C07C 247/08; C08G 61/123; C08G 2261/3228; C08G 2261/334
See application file for complete search history.

(56) References Cited

U.S. PATENT DOCUMENTS 9,290,485 B2    3/2016   Brandl et al.
2016/0272623 A1*   9/2016   Johnson ............... C07D 405/14
2020/0115398 A1    4/2020   Johnson et al.

OTHER PUBLICATIONS

Berge et al, Pharmaceutical salts. J Pharm Sci. Jan. 1977;66(1):1-19.

* cited by examiner

*Primary Examiner* — Shane Fang
(74) *Attorney, Agent, or Firm* — Wolf, Greenfield & Sacks, P.C.

(57) ABSTRACT

Macromolecules comprising triazoles and related compositions and methods are provided. In some embodiments, a macromolecule may comprise one or more repeat units including a triazole and a functionalizable pendant group. The macromolecule may also comprise one or more orthogonally addressable end groups. In some embodiments, one or more repeat units may be formed by a synthetic process that allows for precise control over stereochemistry, pendant functionality, and/or the spatial relationship (e.g., distance) between groups in the repeat unit(s). Such precise control over pendant group and repeat unit structure allows for the macromolecule functionality, stereochemistry, and spacing between groups (e.g., pendant groups) to be precisely controlled. Macromolecules described herein may be used for a wide variety of applications, including the delivery of active agents.

18 Claims, No Drawings

MACROMOLECULES COMPRISING TRIAZOLES AND RELATED COMPOUNDS

RELATED APPLICATIONS

This application claims priority under 35 U.S.C. § 119(e) to U.S. Provisional Application No. 62/740,492, filed Oct. 3, 2018, and entitled "MACROMOLECULES COMPRISING TRIAZOLES AND RELATED COMPOUNDS," which is incorporated herein by reference in its entirety for all purposes.

GOVERNMENT SPONSORSHIP

This invention was made with Government support under Grant No. FA9550-14-1-0292 awarded by the Air Force Office of Scientific Research. The Government has certain rights in the invention.

TECHNICAL FIELD

Macromolecules comprising triazoles and related compositions and methods are provided.

BACKGROUND

Macromolecules are ubiquitous in modern society. In nature, biological systems are capable of synthesizing natural macromolecules with precisely defined length, sequence, and/or stereochemistry. However, precise control over macromolecular structure remains a key challenge in the abiotic synthesis of non-natural macromolecules. Conventional techniques have tried to address this problem by using complex techniques, specialized equipment, costly processes and/or low yield reactions that limit the utility, applicability, and/or scalability of the abiotic synthesis of well-defined non-natural macromolecules. Accordingly, improved compositions and methods are needed.

SUMMARY

Macromolecules comprising triazoles and related compositions and methods are provided. The subject matter of the present invention involves, in some cases, interrelated products, alternative solutions to a particular problem, and/or a plurality of different uses of one or more systems and/or articles.

In one set of embodiments, compounds are provided. In one embodiment, a compound comprises Formula (I):

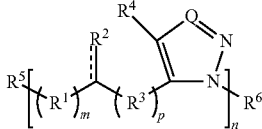

or a salt thereof, wherein:

each Q is independently N or $N^+(R^\#)$ each $R^1$ and $R^3$ is independently O, S, optionally substituted amino, optionally substituted acylene, optionally substituted alkylene, optionally substituted carbocyclylene, optionally substituted heteroalkylene, optionally substituted heterocyclylene, optionally substituted arylene, or optionally substituted heteroarylene;

each $R^2$ is independently O, $OR^\#$, S, $S^\#$, $N(R^\#)$, $N(R^\#)_2$, $C(R^*)_2$, $C(R^*)_3$, $C(=O)R^*$, $C(=NR^{190})R^*$, or $C(=S)^*$;

each ===== is independently a single or double bond, provided that when ===== is a double bond each $R^2$ is independently O, S, $N(R^\#)$, or $C(R^*)_2$, and when ===== is a single bond each $R^2$ is independently $OR^\#$, $SR^\#$, $N(R^\#)_2$, $(C(R^*)_3$, $C(=O)R^*$, $C(=NR^{190})R^*$, or $C(=S)R^*$;

each $R^4$ is independently hydrogen, halo, optionally substituted alkyl, optionally substituted carbocyclyl, optionally substituted heteroalkyl, optionally substituted heterocyclyl, optionally substituted aryl, optionally substituted heteroaryl, or a metal;

$R^5$ is azide, hydroxyl, optionally substituted amino, optionally substituted thiol, optionally substituted acyl, optionally substituted alkyl, optionally substituted carbocyclyl, optionally substituted heteroalkyl, optionally substituted heterocyclyl, optionally substituted alkenyl, optionally substituted heteroalkenyl, optionally substituted aryl, optionally substituted heteroaryl, or an electrophile;

$R^6$ is optionally substituted alkyl, optionally substituted carbocyclyl, optionally substituted heteroalkyl, optionally substituted heterocyclyl, optionally substituted alkenyl, optionally substituted heteroalkenyl, optionally substituted alkynyl, optionally substituted heteroalkynyl, optionally substituted aryl, or optionally substituted heteroaryl;

each $R^\#$ is independently hydrogen, optionally substituted alkyl, optionally substituted carbocyclyl, optionally substituted heteroalkyl, optionally substituted heterocyclyl, optionally substituted alkenyl, optionally substituted heteroalkenyl, optionally substituted aryl, optionally substituted heteroaryl, optionally substituted silyl, or optionally substituted sulfonyl; and each $R^*$ is independently hydrogen, halo, hydroxyl, optionally substituted amino, optionally substituted thiol, optionally substituted acyl, optionally substituted alkyl, optionally substituted carbocyclyl, optionally substituted heteroalkyl, optionally substituted heterocyclyl, optionally substituted alkenyl, optionally substituted heteroalkenyl, optionally substituted aryl, or optionally substituted heteroaryl;

each m and p is independently 0, 1, 2, 3, 4, 5, 6, 7, 8, 9, or 10; and n is an integer between 1 and 500.

In another embodiment, a compound comprises Formula (II):

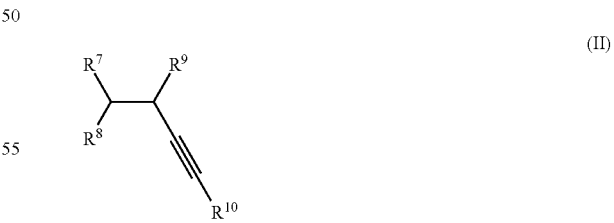

or a salt thereof, wherein:

$R^7$, $R^8$, and $R^9$ are independently hydrogen, azide, or optionally substituted hydroxyl, wherein at least one of $R^7$, $R^8$, and $R^9$ is azide or optionally substituted hydroxyl; and $R^{10}$ is hydrogen or an alkynyl protecting group.

In yet another embodiment, a compound comprises Formula (III):

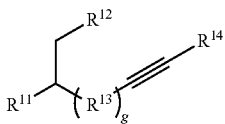

(III)

or a salt thereof, wherein:

$R^{11}$ is independently hydrogen, azide, or optionally substituted hydroxyl; or $R^{12}$ is optionally substituted hydroxyl;

each $R^{13}$ is independently O, S, optionally substituted amino, optionally substituted acylene, optionally substituted alkylene, optionally substituted heteroalkylene, optionally substituted cycloalkylene, optionally substituted heterocycloalkylene, optionally substituted arylene, or optionally substituted heteroarylene;

$R^{14}$ is hydrogen or an alkynyl protecting group; and g is 0, 1, 2, 3, 4, 5, 6, 7, 8, 9, or 10.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

DETAILED DESCRIPTION

Macromolecules comprising triazoles and related compositions and methods are provided. In some embodiments, a macromolecule may comprise one or more repeat units including a triazole and a functionalizable pendant group. The macromolecule may also comprise one or more orthogonally addressable end groups. In some embodiments, one or more repeat units may be formed by a synthetic process that allows for precise control over stereochemistry, pendant functionality, and/or the spatial relationship (e.g., distance) between groups in the repeat unit(s). Such precise control over pendant group and repeat unit structure allows for the macromolecule functionality, stereochemistry, and spacing between groups (e.g., pendant groups) to be precisely controlled. Macromolecules described herein may be used for a wide variety of applications, including the delivery of active agents.

In some embodiments, a macromolecule comprises Formula (I):

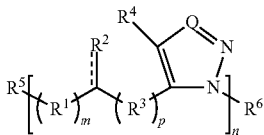

or a salt thereof, wherein:

each Q is independently N or $N^+(R^{190})$ each $R^1$ and $R^3$ is independently O, S, optionally substituted amino, optionally substituted acylene, optionally substituted alkylene, optionally substituted carbocyclylene, optionally substituted heteroalkylene, optionally substituted heterocyclylene, optionally substituted arylene, or optionally substituted heteroarylene;

each $R^2$ is independently O, $OR^\#$, S, $SR^\#$, $N(R^\#)_2$, $C(R^*)_3$, $C(\uparrow O)R^*$, $C(=NR^\#)R^*$, or $C(=S)R^*$;

each ===== is independently a single or double bond, provided that when ===== is a double bond each $R^2$ is independently O, S, $N(R^\#)$, or $C(R^*)_2$, and when ===== is a single bond each $R^2$ is independently $OR^\#$, $SR^\#$, $N(R^{190})_2$, $C(=O)R^*$, $C(=NR^\#)R^*$, or $C(=S)R^*$;

each $R^4$ is independently hydrogen, halo, optionally substituted alkyl, optionally substituted carbocyclyl, optionally substituted heteroalkyl, optionally substituted heterocyclyl, optionally substituted aryl, optionally substituted heteroaryl, or a metal;

$R^5$ is azide, hydroxyl, optionally substituted amino, optionally substituted thiol, optionally substituted acyl, optionally substituted alkyl, optionally substituted carbocyclyl, optionally substituted heteroalkyl, optionally substituted heterocyclyl, optionally substituted alkenyl, optionally substituted heteroalkenyl, optionally substituted aryl, optionally substituted heteroaryl, or an electrophile;

$R^6$ is optionally substituted alkyl, optionally substituted carbocyclyl, optionally substituted heteroalkyl, optionally substituted heterocyclyl, optionally substituted alkenyl, optionally substituted heteroalkenyl, optionally substituted alkynyl, optionally substituted heteroalkynyl, optionally substituted aryl, or optionally substituted heteroaryl;

each $R^\#$ is independently hydrogen, optionally substituted alkyl, optionally substituted carbocyclyl, optionally substituted heteroalkyl, optionally substituted heterocyclyl, optionally substituted alkenyl, optionally substituted heteroalkenyl, optionally substituted aryl, optionally substituted heteroaryl, optionally substituted silyl, or optionally substituted sulfonyl; and each $R^*$ is independently hydrogen, halo, hydroxyl, optionally substituted amino, optionally substituted thiol, optionally substituted acyl, optionally substituted alkyl, optionally substituted carbocyclyl, optionally substituted heteroalkyl, optionally substituted heterocyclyl, optionally substituted alkenyl, optionally substituted heteroalkenyl, optionally substituted aryl, or optionally substituted heteroaryl;

each m and p is independently 0, 1, 2, 3, 4, 5, 6, 7, 8, 9, or 10; and n is an integer between 1 and 500.

In some embodiments, at least one Q is N. In some cases, each Q is N. In some embodiments, at least one Q is $N^+(R^\#)$. In some cases, each Q is $N^+(R^\#)$. In certain embodiments, at least one Q is N and at least one Q is $N^+(R^\#)$. In some embodiments, at least one ===== is a single bond. In some cases, each ===== is a single bond. In some embodiments, at least one ===== is a double bond. In certain embodiments, at least one ===== is a single bond and at least one ===== is a double bond. In some embodiments, each $R^2$ is independently 0, $OR^\#$, S, $SR^\#$, $N(R^\#)$, or N(102.

In some such cases, each $R^2$ is independently S or $SR^\#$. In other cases, each $R^1$ is independently O, $OR^\#$, $N(R^\#)$, or $N(R^\#)_2$ In some embodiments, each $R^2$ is independently S, $SR^\#$, $C(R^*)_2$, $C(R^*)_3$, $C(=O)R^*$, $C(=NR^{190})R^*$, or $C(=S)R^*$. In certain embodiments, each $R^2$ is independently $C(R^*)_2$, $C(R^*)_3$, $C(=O)R^*$, $C(=NR^\#)R^*$, or $C(=S)R^*$. For instance, in some embodiments, at least one $R^2$ is $C(R^*)_2$ or $C(R^*)_3$. In some cases, at least one (e.g., each) $R^2$ is $C(R^*)_3$. In some such cases, at least one $R^*$ is optionally substituted heteroalkyl, optionally substituted heteroalkenyl, optionally substituted heteroalkynyl, or optionally substituted heterocyclyl.

In some embodiments, at least one (e.g., each) $R^2$ is $C(R^*)_3$ and has the structure:

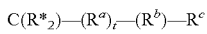

wherein:

each $R^a$ is independently optionally substituted alkylene, optionally substituted alkenylene, or optionally substituted alkynylene;

$R^b$ is O, N(R), or S;

$R^c$ is hydrogen, optionally substituted acyl, optionally substituted alkyl, optionally substituted carbocyclyl, optionally substituted heteroalkyl, optionally substituted alkenyl, optionally substituted heteroalkenyl, optionally substituted alkynyl, optionally substituted heteroalkynyl, optionally substituted heterocyclyl, optionally substituted aryl, optionally substituted heteroaryl, optionally substituted silyl, or optionally substituted sulfonyl;

R is hydrogen or optionally substituted alkyl; and t is 0, 1, 2, 3, 4, 5, 6, 7, 8, 9, or 10.

In some such cases, each IV is optionally substituted alkylene and/or RC is hydrogen, optionally substituted acyl, optionally substituted alkyl, optionally substituted alkenyl, optionally substituted alkynyl, optionally substituted aryl, optionally substituted silyl, or optionally substituted sulfonyl. In some cases, RC is hydrogen, optionally substituted alkyl, heteroalkyl, optionally substituted silyl, or optionally substituted sulfonyl. In some instances, RC is hydrogen, optionally substituted alkyl, optionally substituted silyl, or optionally substituted sulfonyl. In some cases, $R^b$ is O or N(R). In some instances, $R^b$ is O. In some cases, t is 0, 1, 2, 3, 4, or 5 (e.g., 0, 1, 2, or 3). In some instances, t is 1, 2, 3, 4, or 5 (e.g., 1, 2, or 3).

In certain embodiments when at least one (e.g., each) $R^2$ is $C(R^*)_3$ and has the structure $C(R^*_2)\text{—}(R^a)_t\text{—}(R^b)\text{—}R^c$:

each $R^a$ is independently optionally substituted alkylene;

$R^b$ is O or N(R);

$R^c$ is hydrogen, optionally substituted alkyl, heteroalkyl, optionally substituted silyl, or optionally substituted sulfonyl;

R is hydrogen or optionally substituted alkyl; and t is 0, 1, 2, 3, 4, or 5.

In some embodiments, each $R^\#$ is independently hydrogen, optionally substituted alkyl, optionally substituted carbocyclyl, optionally substituted heteroalkyl, optionally substituted heterocyclyl, optionally substituted aryl, optionally substituted heteroaryl, optionally substituted silyl, or optionally substituted sulfonyl. In some such cases, each $R^\#$ is independently hydrogen, optionally substituted alkyl, optionally substituted heteroalkyl, optionally substituted heterocyclyl, optionally substituted aryl, optionally substituted heteroaryl, optionally substituted silyl, or optionally substituted sulfonyl. In certain embodiments, each $R^\#$ is independently hydrogen, optionally substituted alkyl, optionally substituted silyl, or optionally substituted sulfonyl. For instance, in some embodiments, at least one (e.g., each) $R^2$ is $OR^\#$ and each $R^\#$ is independently hydrogen, optionally substituted alkyl, optionally substituted silyl, or optionally substituted sulfonyl. In certain cases, at least one (e.g., each) $R^2$ is $OR^\#$ and each $R^\#$ is independently optionally substituted silyl, or optionally substituted sulfonyl.

In some embodiments in which at least one (e.g., each) $R^\#$ is $C(R^*)_2$, $C(R^*)_3$, $C(=O)R^*$, $C(=NR^\#)R^*$, or $C(=S)R^*$, each $R^*$ is independently hydrogen, optionally substituted hydroxyl, optionally substituted amino, optionally substituted thiol, optionally substituted acyl, optionally substituted alkyl, optionally substituted carbocyclyl, optionally substituted heteroalkyl, optionally substituted alkenyl, optionally substituted heteroalkenyl, optionally substituted alkynyl, optionally substituted heteroalkynyl, or optionally substituted heterocyclyl. In some cases, each $R^*$ is independently hydrogen, optionally substituted alkyl, optionally substituted hydroxyl, optionally substituted amino, or optionally substituted thiol, wherein $R^6$ is optionally substituted with one or more alkyl, alkenyl, alkynl, aryl, silyl, or sulfonyl. In certain embodiments, at least one $R^*$ is optionally substituted hydroxyl, optionally substituted amino, or optionally substituted thiol. In some such embodiments, $R^*$ is optionally substituted with one or more optionally substituted alkyl, alkenyl, alkynl, aryl, silyl, or sulfonyl.

In some embodiments when at least one (e.g., each) $R^2$ is $C(R^*)_3$ and has the structure $C(R^*_2)\text{-}(R^a)_t\text{-}(R^b)\text{-}R^c$, each $R^*$ is independently hydrogen, optionally substituted alkyl, optionally substituted carbocyclyl, optionally substituted heteroalkyl, or optionally substituted heterocyclyl. In some such cases, each $R^*$ is independently hydrogen, optionally substituted alkyl, or optionally substituted heteroalkyl. In some instances, each $R^*$ is independently hydrogen or optionally substituted alkyl.

In some embodiments, each $R^1$ and $R^3$ is independently O, S, optionally substituted amino, optionally substituted alkylene, or optionally substituted heteroalkylene. In some cases, each $R^1$ and $R^3$ is independently O, optionally substituted amino, or optionally substituted alkylene. For instance, in some embodiments, each $R^1$ and $R^3$ is independently O—, —$CH_2$—, or N(R)—. In some embodiments, each $(R^1)_m$ and $(R^3)_p$ is independently $CH_2$, $OCH_2$, $CH_2O$, $N(R)CH_2$, $CH_2N(R)$, or $CH_2OCH_2$. For example, in some embodiments, Formula (I) has the structure:

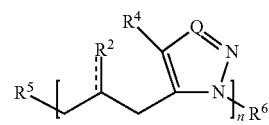

or a salt thereof, wherein Q, $R^2$, $R^4$, $R^5$, $R^6$, ══════ and n are as described herein. As another example, in some embodiments, Formula (I) has the structure:

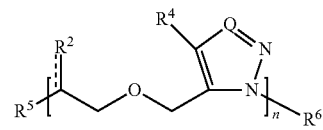

or a salt thereof, wherein Q, $R^2$, $R^4$, $R^5$, $R^6$, ══════, and n are as described herein. For instance, $R^2$ may be $C(R^*)_3$ as described herein.

In some embodiments, each m and p is independently 0, 1, 2, 3, 4, or 5. For instance, in some embodiments, m and p are independently 0, 1, 2, or 3. In certain embodiments, m and/or p is zero. For example, m is 0 and p is greater than 0 (e.g., 1, 2, or 3). In some such cases, Formula (I) has the structure:

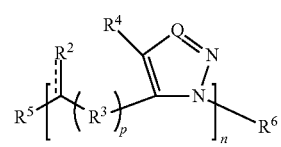

or a salt thereof, wherein Q, $R^2$, $R^3$, $R^4$, $R^5$, $R^6$, ≈≈≈≈≈, p, and n are as described herein. For instance, $R^2$ may be $C(R^*)_3$ as described herein. Each $R^3$ may independently be —O—, —CH$_2$—, or N(R)—. In some cases, Formula (I) has the structure:

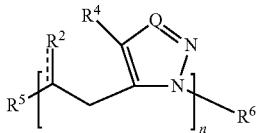

or a salt thereof, wherein Q, $R^2$, $R^4$, $R^5$, $R^6$, ≈≈≈≈≈, and n are as described herein. For instance, $R^2$ may be $C(R^*)_3$ as described herein.

As another example, p is 0 and m is greater than 0 (e.g., 1, 2, or 3). In some such cases, Formula (I) has the structure:

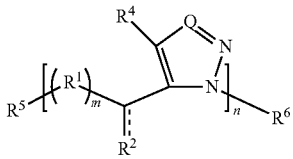

or a salt thereof, wherein Q, $R^1$, $R^2$, $R^4$, $R^5$, $R^6$, ≈≈≈≈≈, m, and n are as described herein. For instance, $R^2$ may be $C(R^*)_3$ as described herein. Each $R^1$ may independently be —O—, —CH$_2$—, or N(R)—. In some cases, Formula (I) has the structure:

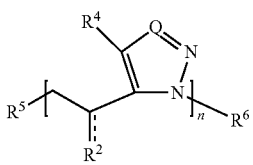

or a salt thereof, wherein Q, $R^2$, $R^4$, $R^5$, $R^6$, ≈≈≈≈≈, and n are as described herein. For instance, $R^2$ may be $C(R^*)_3$ as described herein.

In some embodiments, each m and p is independently 0 or 1. In some such cases, Formula (I) has the structure:

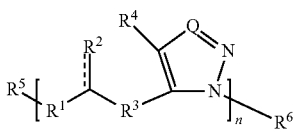

or a salt thereof, wherein Q, $R^1$, $R^2$, $R^3$, $R^4$, $R^5$, $R^6$, ≈≈≈≈≈, m and n are as described herein. Each $R^1$ and $R^3$ may independently be —O—, —CH$_2$—, or N(R)—. As another example, Formula (I) has the structure:

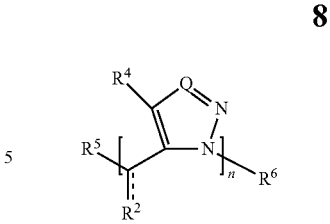

or a salt thereof, wherein Q, $R^2$, $R^4$, $R^5$, $R^6$, ≈≈≈≈≈, and n are as described herein. For instance, $R^2$ may be $C(R^*)_3$ as described herein.

In some embodiments, each $R^4$ is independently hydrogen, halo, optionally substituted alkyl, optionally substituted carbocyclyl, optionally substituted heteroalkyl, optionally substituted heterocyclyl, optionally substituted aryl, or optionally substituted heteroaryl. In certain embodiments, at least one (e.g., each) $R^4$ is hydrogen, optionally substituted alkyl, optionally substituted heteroalkyl, optionally substituted aryl, or optionally substituted heteroaryl. In some instances, at least one $R^4$ is a metal. In some embodiments, each $R^4$ is hydrogen or optionally substituted alkyl. In some cases, each $R^4$ is hydrogen.

As noted above, $R^5$ and $R^6$ are independently an end group. Non-limiting examples of end groups for use in the compounds and methods described herein include metal coordinating ligand, active agents, functionalizable groups, oligomers, and polymers (e.g., polymer block). In some embodiments, at least one end group may comprise an active agent (e.g., a drug). In some embodiments, at least one end group may comprise a peptide, protein, carrier, or other group that provides biocompatibility to the molecule. In some embodiments, at least one end group may be attached to a particle (e.g., inorganic particle). In some embodiments, the funtionalizable end group is a polymerizable group. In some embodiments, each end group comprises a functionalizable group.

In some embodiments, an end group may comprise a polymerizable functional group. The end group may comprise the polymerizable functional group and a linking group attaching the polymerizable group to the macromolecule. In some embodiments, the polymerizable functional group may comprise one or more of an alkenyl groups, cycloalkenyl group, carboxyl group, amide group, alcohol group, epoxide group, isocyanate group, etc. In some embodiments, the polymerizable group comprises a cycloalkenyl group which may be polymerized, for example, via ring opening metathesis polymerization (ROMP). A non-limiting example of an end group that may be polymerized via ROMP is norbornene. In some embodiments, the polymerizable end group may be polymerized using a polymerization reaction to form a brush polymer. Polymerization reactions may comprise one or more of step growth, chain growth, free radical, anionic, cationic, ring opening, and ring opening metathesis polymerization reactions. In some embodiments, the polymerization reaction may comprise exposure to one or more of an initiator, a catalyst, one or more solvents, heat, light, and an oxygen- and/or moisture-free environment. In some embodiments, the polymerization reaction may comprise exposure to none of these things. In some embodiments, an end group comprising norbornene may undergo a ring opening metathesis polymerization reaction.

The polymers formed from via the polymerization of the end groups may be one or more of isotactic polymers, atactic polymers, and block copolymers. In some embodiments, the polymerization may be carried out on macromolecules comprising a certain stereochemistry. For example, the macromolecule may comprise all R configurations, all S configurations, or alternating R/S configurations. The selection of macromolecules can be tailored to form the desired tacticity of the resulting polymer. For example, in embodiments wherein the macromolecules comprise all R, all S, or all R/S configurations, the resulting polymer will be isotatic. As another example, an atactic polymer maybe formed utilizing a mixture of macromolecules having different stereochemistries (e.g., a mixture of R, S, and/or R/S macromolecules). As yet another example, a block copolymer may be formed by providing macromolecules having different stereochemistries sequentially (e.g., first provide all R, then all S; first provide all R, then R/S; first provide all S, then R; first provide all S, then R/s; first provide all R/S, then R; first provide all R/S, then S).

In some embodiments, $R^5$ is azide, halo, optionally substituted hydroxyl, optionally substituted amino, optionally substituted thiol, optionally substituted acyl, optionally substituted alkyl, optionally substituted carbocyclyl, optionally substituted heteroalkyl, optionally substituted alkenyl, optionally substituted heteroalkenyl, optionally substituted heterocyclyl, optionally substituted aryl, optionally substituted heteroaryl, optionally substituted sulfonyl, or an electrophile. In some cases, $R^5$ is azide, halo, optionally substituted hydroxyl, optionally substituted amino, optionally substituted thiol, optionally substituted acyl, optionally substituted alkyl, optionally substituted carbocyclyl, optionally substituted heteroalkyl, optionally substituted alkenyl, optionally substituted heteroalkenyl, optionally substituted heterocyclyl, optionally substituted aryl, optionally substituted heteroaryl, or optionally substituted sulfonyl.

In some embodiments, $R^5$ is a functionalizable group. In some such cases, $R^5$ is azide, halo, optionally substituted hydroxyl, optionally substituted amino, optionally substituted thiol, optionally substituted acyl, optionally substituted heteroalkyl, optionally substituted alkenyl, optionally substituted heteroalkenyl, optionally substituted heterocyclyl, optionally substituted aryl, optionally substituted heteroaryl, optionally substituted sulfonyl, or an electrophile. In some instances, $R^5$ is azide, halo, optionally substituted hydroxyl, optionally substituted amino, optionally substituted thiol, optionally substituted acyl, optionally substituted heteroalkyl, optionally substituted alkenyl, optionally substituted heteroalkenyl, optionally substituted heterocyclyl, optionally substituted aryl, optionally substituted heteroaryl, or optionally substituted sulfonyl. In certain cases, $R^5$ is halo, optionally substituted heterocyclyl, optionally substituted heteroaryl, optionally substituted sulfonyl, or an electrophile.

In some embodiments, $R^5$ is an electrophile. As used herein, the term "electrophile" has its ordinary meaning in the art and may refer to a group that forms a bond to its reaction partner (e.g., the nucleophile) by accepting both bonding electrons from that reaction partner. In some embodiments, the electrophile is a Lewis acid. In some embodiments, the electrophile has an electrophilicity index (ω) of greater than or equal to about 0.8, greater than or equal to about 1.0, greater than or equal to about 1.2, greater than or equal to about 1.5, greater than or equal to about 1.8, greater than or equal to about 2.0, greater than or equal to about 2.2, greater than or equal to about 2.5, greater than or equal to about 2.8, greater than or equal to about 3.0, greater than or equal to about 3.2, greater than or equal to about 3.5, greater than or equal to about 3.8, greater than or equal to about 4.0, or greater than or equal to about 4.2. In some instances, the electrophilicity index (ω) of the electrophile is less than or equal to about 4.5, less than or equal to about 4.2, less than or equal to about 4.0, less than or equal to about 3.8, less than or equal to about 3.5, less than or equal to about 3.2, less than or equal to about 3.0, less than or equal to about 2.8, less than or equal to about 2.5, less than or equal to about 2.2, less than or equal to about 2.0, less than or equal to about 1.8, less than or equal to about 1.5, less than or equal to about 1.2, or less than or equal to about 1.0. Combinations of the above-referenced ranges are also possible (e.g., greater than or equal to about 0.8 and less than or equal to about 4.5, e.g., greater than or equal to about 1 and less than or equal to about 2.5). Non-limiting example of suitable electrophiles include halo,

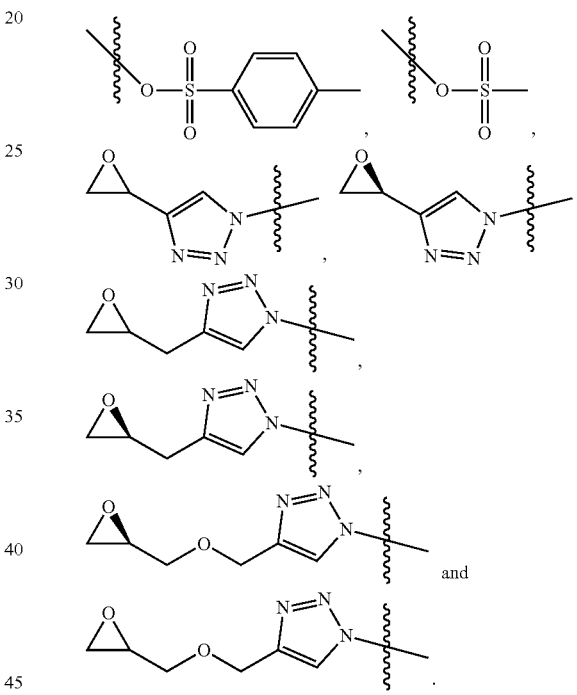

In some embodiments, the electrophile may be relatively enantiopure (e.g., enantiomeric excess of greater than about 50%, greater than about 80%, or greater than about 95%).

In some embodiments, $R^6$ is optionally substituted alkyl, optionally substituted carbocyclyl, optionally substituted heteroalkyl, optionally substituted alkenyl, optionally substituted heteroalkenyl, optionally substituted alkynyl, optionally substituted heteroalkynyl, optionally substituted heterocyclyl, optionally substituted aryl, or optionally substituted heteroaryl. In certain embodiments, $R^6$ is a functionalizable group. In some such cases, $R^6$ is optionally substituted heteroalkyl, optionally substituted alkenyl, optionally substituted heteroalkenyl, optionally substituted alkynyl, optionally substituted heteroalkynyl, optionally substituted heterocyclyl, or optionally substituted heteroaryl. In certain embodiments, $R^6$ is optionally substituted alkynyl or optionally substituted heteroalkynyl. For instance, in some embodiments, $R^6$ is selected from the group consisting of:

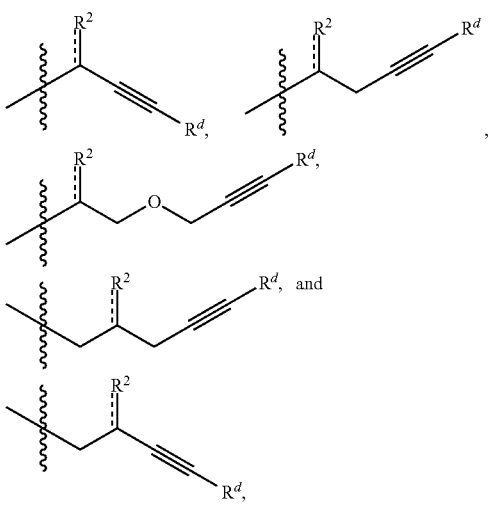

wherein $R^2$ and ----- are as described herein and $R^d$ is hydrogen, optionally substituted alkyl, optionally substituted carbocyclyl, optionally substituted heteroalkyl, optionally substituted heterocyclyl, optionally substituted aryl, or optionally substituted heteroaryl, or optionally substituted silyl. In some instances, $R^d$ is hydrogen or optionally substituted silyl In some embodiments, n is 2-500, 3-500, 10-500, 16-500, 32-500, 50-500, 100-500, 2-400, 3-400, 10-400, 16-400, 32-400, 50-400, 100-400, 2-300, 3-300, 10-300, 16-300, 32-300, 50-300, 100-300, 2-200, 3-200, 10-200, 16-200, 32-200, 50-200, 100-200, 2-100, or 2-50.

In some embodiments for a compound of Formula (I):

each $R^2$ is independently OR', SR', N(R')$_2$, C(R'')$_3$, C(=O)R'', C(=NR')R'', or C(=S)R'';

each ----- is a single bond;

each $R^1$ and $R^3$ is independently O, optionally substituted amino, or optionally substituted alkylene;

each $R^4$ is independently hydrogen, optionally substituted alkyl, or a metal;

each $R^\#$ is independently hydrogen, optionally substituted alkyl, optionally substituted silyl, or optionally substituted sulfonyl;

each $R^*$ is independently hydrogen, optionally substituted hydroxyl, optionally substituted amino, optionally substituted thiol, optionally substituted alkyl, or optionally substituted heteroalkyl;

n is an integer between 2 and 500; and

Q, m, p, $R^5$, and $R^6$ are as described herein.

In some embodiments for a compound of Formula (I):

each $R^2$ is independently OR', N(R')$_2$, or C(R'')$_3$,;

each ----- is a single bond;

each $R^1$ and $R^3$ is independently O, optionally substituted amino, or optionally substituted alkylene;

each $R^4$ is independently hydrogen, optionally substituted alkyl, or a metal;

each $R^\#$ is independently hydrogen, optionally substituted alkyl, optionally substituted silyl, or optionally substituted sulfonyl;

each $R^*$ is independently hydrogen, optionally substituted hydroxyl, optionally substituted amino, optionally substituted thiol, optionally substituted alkyl, or optionally substituted heteroalkyl;

each m and p is independently 0, 1, 2, or 3;

n is an integer between 2 and 500; and

Q, $R^5$, and $R^6$ are as described herein.

In one aspect, methods are provided. In some embodiments, a method may comprise reacting a precursor molecule comprising an optionally substituted hydroxyl (e.g., protected hydroxyl) with an azide source to form a monomer comprising the azide. In some embodiments, the precursor compound may also comprise an optionally substituted alkynyl group (e.g., protected alkynyl). In some such embodiments, the monomer comprising the azide may also comprise an optionally substituted alkyne.

Those of ordinary skill in the art will be aware of conditions and reagents for carrying out such a reaction, for example, reacting the molecule comprising the epoxide with an azide source. Non-limiting examples of azide sources include trialkylammonium azide, a tetraalkylammonium azide, ammonium azide, lithium azide, sodium azide, potassium azide, rubidium azide, cesium azide, beryllium azide, magnesium azide, calcium azide, strontium azide, barium azide, or combinations thereof.

In some embodiments, the precursor molecule and the monomer may be of Formula

(II)

or a salt thereof, wherein:

$R^7$, $R^8$, and $R^9$ are independently hydrogen, azide, or optionally substituted hydroxyl, wherein at least one of $R^7$, $R^8$, and $R^9$ is azide or optionally substituted hydroxyl; and $R^{10}$ is hydrogen or an alkynyl protecting group.

In some embodiments, for a precursor molecule of Formula (II):

$R^7$, $R^8$, and $R^9$ are independently hydrogen or optionally substituted hydroxyl, wherein at least one of $R^7$, $R^8$, and $R^9$ is optionally substituted hydroxyl; and $R^{10}$ is hydrogen or an alkynyl protecting group.

In some embodiments, at least one of $R^7$ and $R^8$ is optionally substituted hydroxyl. In certain embodiments, at least one of $R^7$ and $R^9$ is optionally substituted hydroxyl. In some cases, at least one of $R^8$ and $R^9$ is optionally substituted hydroxyl. In some embodiments, at least two of $R^7$, $R^8$, and $R^9$ is optionally substituted hydroxyl. In certain embodiments, at least one of $R^7$, $R^8$, and $R^9$ is hydrogen. In some embodiments in which at least one (e.g., one, two) of $R^7$, $R^8$, and $R^9$ is optionally substituted hydroxyl, the hydroxyl is optionally substituted with an oxygen protecting group.

In some embodiments, at least one of $R^7$, $R^8$, and $R^9$ is a substituted hydroxyl. In such embodiments, the substituted hydroxyl may be a suitable leaving group (e.g., tosylate, mesylate) for the reaction with the azide source. Those of ordinary skill in the art will be aware of suitable leaving groups. In some embodiments, the substituted hydroxyl is a protected hydroxyl having the structure O-PG, wherein PG is a protecting group. In some embodiments, the protecting group is a silyl group or a heteroalkyl group.

In some embodiments, for a monomer of Formula (II):

$R^7$, $R^8$, and $R^9$ are independently hydrogen, azide, or optionally substituted hydroxyl, wherein at least one of $R^7$, $R^8$, and $R^9$ is an azide; and $R^{10}$ is hydrogen or an alkynyl protecting group.

In some embodiments, at least one (e.g., one) of $R^7$ and $R^8$ is an azide. In certain embodiments, at least one (e.g., one) of $R^7$ and $R^9$ is an azide. In some cases, at least one (e.g., one) of $R^8$ and $R^9$ is an azide.

In certain embodiments, at least one (e.g., one, two) of $R^7$, $R^8$, and $R^9$ is hydrogen or optionally substituted hydroxyl. In some embodiments in which at least one (e.g., one, two) of $R^7$, $R^8$, and $R^9$ is optionally substituted hydroxyl, the hydroxyl is optionally substituted with an oxygen protecting group. In some embodiments, the protecting group is a silyl group or a heteroalkyl group.

In some embodiments, the precursor molecule and the monomer may be of Formula (III).

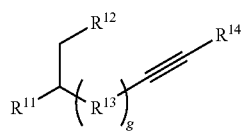

(III)

or a salt thereof, wherein:

$R^{11}$ is independently hydrogen, azide, or optionally substituted hydroxyl;

$R^{12}$ is optionally substituted hydroxyl;

each $R^{13}$ is independently O, S, optionally substituted amino, optionally substituted acylene, optionally substituted alkylene, optionally substituted heteroalkylene, optionally substituted cycloalkylene, optionally substituted heterocycloalkylene, optionally substituted arylene, or optionally substituted heteroarylene;

$R^{14}$ is hydrogen or an alkynyl protecting group; and g is 0, 1, 2, 3, 4, 5, 6, 7, 8, 9, or 10.

In some embodiments, for a precursor molecule of Formula (III):

$R^{11}$ is independently hydrogen or optionally substituted hydroxyl;

$R^{12}$ is optionally substituted hydroxyl;

each $R^{13}$ is independently O, S, optionally substituted amino, optionally substituted acylene, optionally substituted alkylene, optionally substituted heteroalkylene, optionally substituted cycloalkylene, optionally substituted heterocycloalkylene, optionally substituted arylene, or optionally substituted heteroarylene;

$R^{14}$ is hydrogen or an alkynyl protecting group; and g is 0, 1, 2, 3, 4, 5, 6, 7, 8, 9, or 10.

In some embodiments, R" is optionally substituted hydroxyl. In certain embodiments, $R^{14}$ is hydrogen. In some embodiments in which $R^{11}$ and/or $R^{12}$ is optionally substituted hydroxyl, the hydroxyl is optionally substituted with an oxygen protecting group.

In some embodiments, at least one (e.g., one, both) of $R^{11}$ and $R^{12}$ is a substituted hydroxyl. In such embodiments, the substituted hydroxyl may be a suitable leaving group (e.g., tosylate, mesylate) for the reaction with azide source. Those of ordinary skill in the art will be aware of suitable leaving groups. In such embodiments, the substituted hydroxyl is a protected hydroxyl having the structure O-PG, wherein PG is a protecting group. In some embodiments, the protecting group is a silyl group or a heteroalkyl group.

In some embodiments, g is 1, 2, 3, 4, 5, 6, 7, 8, 9, or 10. In some instances, g is 1, 2, 3, 4, or 5 (e.g., 1, 2, or 3). In some case, g is not 0. In certain embodiments, g is 0, 1, 2, 3, 4, 5, 6, 7, 8, 9, or 10. In some such cases, g is 0, 1, 2, 3, 4, or 5 (e.g., 0, 1, 2, 3, or 5).

In some embodiments, for a monomer of Formula (III):

$R^{11}$ is an azide;

$R^{12}$ optionally substituted hydroxyl;

each $R^{13}$ is independently O, S, optionally substituted amino, optionally substituted acylene, optionally substituted alkylene, optionally substituted heteroalkylene, optionally substituted cycloalkylene, optionally substituted heterocycloalkylene, optionally substituted arylene, or optionally substituted heteroarylene;

$R^{14}$ is hydrogen or an alkynyl protecting group; and g is 0, 1, 2, 3, 4, 5, 6, 7, 8, 9, or 10.

In some embodiments, $R^{12}$ is a substituted hydroxyl. In some such embodiments, the substituted hydroxyl is a protected hydroxyl having the structure O-PG, wherein PG is a protecting group. In some embodiments, the protecting group is a silyl group or a heteroalkyl group. In some embodiments, g is 1, 2, 3, 4, 5, 6, 7, 8, 9, or 10. In some instances, g is 1, 2, 3, 4, or 5 (e.g., 1, 2, or 3). In some case, g is not 0. In certain embodiments, g is 0, 1, 2, 3, 4, 5, 6, 7, 8, 9, or 10. In some such cases, g is 0, 1, 2, 3, 4, or 5 (e.g., 0, 1, 2, 3, or 5).

In some embodiments, a chiral compound of Formula (II) and/or a chiral compound of Formula (III) may be prepared (e.g., see the Examples). As a non-limiting example, in some embodiments, Formula (II) may have the structure:

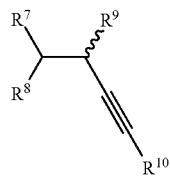

or a salt thereof, wherein $R^7$, $R^8$, $R^9$, and $R^{10}$ are as described herein, and $R^9$ may be oriented to provide an R or S stereochemistry at the carbon center indicated by an asterisk. In some embodiments, the *carbon center has an S configuration. In some embodiments, the *carbon has an R configuration.

As another example, Formula (III) may have the structure:

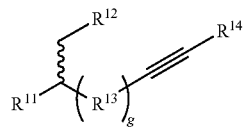

or a salt thereof, wherein $R^{11}$, $R^{12}$, $R^{13}$, $R^{14}$, and g are as described herein, and the $R^9$ may be oriented to provide an R or S stereochemistry at the carbon center indicated by an asterisk. In some embodiments, the *carbon center has an S configuration. In some embodiments, the *carbon has an R configuration. Those of ordinary skill in the art will be able to apply these teachings to the macromolecules and repeat units described herein.

In some embodiments, a precursor molecule and/or monomer of Formula (II) and/or Formula (III) may be prepared having an enantiomeric excess greater than about 50%, greater than about 60%, greater than about 70%, greater than about 80%, greater than about 90%, greater than about 95%, greater than about 98%, or greater than about 99%. In some embodiments, the stereochemistry of the precursor molecule and/or monomer may be retained during the formation of the macromolecule. In some such cases, the macromolecule may be formed with specific stereochemistry. For example, in some embodiments, isotactic macromolecules, atactic macromolecules, syndiotactic macromolecules, stereoblock macromolecules, and stereoregular macromolecules may be formed.

In some embodiments, the method involves a coupling reaction in which monomers and/or oligomers are joined together via one or more covalent bonds. Non-limiting examples of suitable coupling reactions include cycloaddition reactions, imine condensation, Michael additions, and click chemistry. For example, the method may involve a click chemistry reaction, for example, between a precursor molecule comprising an optionally substituted alkynyl (e.g., precursor molecule of Formula (II), precursor molecule of Formula (III)) and a monomer comprising an azide (e.g., monomer of Formula (II), monomer of Formula (III)). Those of ordinary skill in the art will be aware of conditions and reagents for carrying out a click chemistry reaction. For example, click chemistry reaction may be carried out in the presence of one or more additives, such as a catalyst (e.g., ruthenium catalyst). Methods for performing click chemistry reactions are described, for example, in Synthetic Applications of 1,3-Dipolar Cycloaddition Chemistry Toward Heterocycles and Natural Products, A. Padwa, W. H. Pearson, Wiley-Interscience, 2002; Iha et al., Chem. Rev. 109, 11, 5620-5686; Meldal et al., Chem. Rev. 108, 8, 2952-3015; De Bruycker et al., Chem. Rev. 116, 6, 3919-3974; and Jewett et al., Chem. Soc. Rev., 2010,39, 1272-1279 the contents of each of which are incorporated herein by reference. In some embodiments, the click chemistry reaction may be carried out in the presence of a copper catalyst. Those of ordinary skill in the art will be aware of suitable reagents and conditions for carrying out a click chemistry reaction (e.g., $CpRuCl(PPh_3)_2$, $Ru(OAc)_2(PPh_3)_2$, $RuCl_2(PPh_3)_3$, $Cp^*RuCl(COD)$). In some embodiments, monomers may be polymerized using click chemistry to form a macromolecule.

Those of ordinary skill in the art will be aware of suitable alkyne protecting groups (e.g., see "Protective Groups in Organic Synthesis", Theodora W. Greene and Peter G. M. Wuts, Chapter 8, pages 927-933, 4th edition (John Wiley & Sons, 2007)) for the compounds and methods described herein. Non-limiting examples of alkyne protecting groups comprise groups comprising trialkylsilyl groups. For example, non-limiting examples of alkyne protecting groups include trialkylsilyl groups where each alkyl group is independently alkyl, aryldialkylsilyl groups where the aryl group (e.g., benzyl, biphenyl) and the alkyl groups are independently alkyl, hydroxymethyl, or 2-(2-hydroxypropyl). In some embodiments, the alkyne protecting group is tert-butyldimethylsilyl. Another example of a non-limiting protecting group includes trialkylsilyl ether protecting groups. In some embodiments, the protecting group is triisopropylsilyl ether (TIPS).

Those of ordinary skill in the art will be aware of conditions and reagents for carrying out the synthetic methods described herein.

In some embodiments, a method comprises deprotecting an alkyne group. Those of ordinary skill in the art will be aware of conditions and reagents for deprotecting an alkyne group, for example, via reaction with tetrabutylammonium fluoride or another deprotecting reagent.

Any suitable solvent may be utilized in the synthetic methods described herein. Non-limiting examples of solvents include water, methanol, ethanol, propanol, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide (DMSO), dimethylformamide, hexamethyl-phosphoric triamide, ethyl acetate, pyridine, triethylamine, picoline, mixtures thereof, or the like.

The methods of synthesis described herein may be carried out at any suitable temperature. In some cases, the reaction is carried out at about room temperature (e.g., about 25° C., about 20° C., between about 20° C. and about 25° C., or the like). In some cases, however, the reaction is carried out at temperatures below or above room temperature. In some embodiments, the reaction is carried out a temperature between about 0° C. and about 25° C. In some embodiments, the reaction is carried at a temperature between about 25° C. and about 200° C., about 25° C. and about 150° C., or between about 50° C. and about 200° C., or between about 50° C. and about 150° C., or between about 100° C. and about 150° C.

In some embodiments, the synthetic methods may be carried out in a flow reactor. Flow reactors will be known to those of ordinary skill in the art. Flow reactors may be provided in various configurations and may be equipped with a number of components to utilize methods described herein. Non-limiting components of a flow reactor include inlet(s) (e.g., for reactants, solvents, quenching agents, etc.), reaction tube and/or chamber (e.g., where the reaction occurs), outlet(s), pressure controller(s) (e.g., back pressure regulators), and temperature control device(s) (e.g., heating device(s) and/or cooling device(s)).

In some embodiments, an iterative functional exponential growth process may be used to form the macromolecule as described herein. Non-limiting examples of suitable iterative growth processes can be found in International Application No. PCT/US2016/023201, filed Mar. 18, 2016, entitled "Formation of Macromolecules Using Iterative Growth and Related Compounds," by Johnson, et al., which is incorporated by reference in its entirety for all purposes.

As noted above, in some embodiments, the stereochemistry of the pendant groups present in the macromolecules may be precisely controlled. In some embodiments, the pendant group may be attached to the backbone via an asymmetric atom (e.g., asymmetric carbon atom). In some such cases, the stereochemistry of the pendant group may be selected and/or controlled to produce a macromolecule with a well-defined stereochemistry. In some embodiments, isotactic macromolecules, atactic macromolecules, syndiotactic macromolecules, stereoblock macromolecules, and stereoregular macromolecules may be formed (e.g., via an iterative functional exponential growth process). In some embodiments, each of the pendant groups may be present on the same side of the macromolecule, on alternating sides of the macromolecule, or some other sequence. For example, non-limiting examples of suitable stereochemistry of the pendant groups are shown below, wherein each FG represents a pendant group and ⁓ represents the backbone of the macromolecule:

-continued

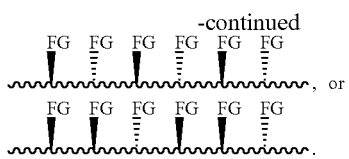

In some embodiments, the degree of tacticity of the macromolecules formed via an iterative functional exponential growth process may be greater than about 50%, greater than about 60%, greater than about 70%, greater than about 80%, greater than about 90%, greater than about 95%, greater than about 98%, or greater than about 99%.

In some embodiments, macromolecules, described herein, may have a relatively uniform mass. In some instances, the average molecular weights and their ratios may be used to characterize the breadth of the molecular weight distribution of the polymer composition. For instance, in some embodiments, the dispersity index ($W_w/M_n$) may be used to describe the breadth of the molecular weight distribution. In some embodiments, the dispersity index of the macromolecules may be about 1. That is, all of the macromolecules present in a sample may have the same length. In other embodiments, the dispersity index of the macromolecules may be less than or equal to about 2, less than or equal to about 1.9, less than or equal to about 1.8, less than or equal to about 1.7, less than or equal to about 1.6, less than or equal to about 1.5, less than or equal to about 1.4, less than or equal to about 1.3, less than or equal to about 1.2, less than or equal to about 1.15, less than or equal to about 1.1, less than or equal to about 1.08, less than or equal to about 1.06, less than or equal to about 1.04, less than or equal to about 1.02, less than or equal to about 1.01, or equal to 1.0 . The dispersity index may be measured for a sample after none or one or more purification steps.

In some embodiments, the macromolecules may have any suitable number of repeat units (e.g., integer between 2 and 500). For instance, the number of repeat units in the first component may be greater than or equal to about 2, greater than or equal to about 4, greater than or equal to about 8, greater than or equal to about 16, greater than or equal to about 32, greater than or equal to about 50, greater than or equal to about 100, greater than or equal to about 200, greater than or equal to about 300, or greater than or equal to about 400. In some instances, the number of repeat units in the first component may be less than or equal to about 500, less than or equal to about 400, less than or equal to about 300, less than or equal to about 200, less than or equal to about 100, less than or equal to about 64, less than or equal to about 50, less than or equal to about 32, or less than or equal to about 16. Combinations of the above-referenced ranges are also possible (e.g., greater than or equal to about 16 and less than or equal to about 500). Other values of the number of repeat units in the first component are also possible. The number of repeat units may be determined using gel permeation chromatography (GPC), nuclear magnetic resonance (NMR), or may be obtained from a manufacturer's specifications.

In some embodiments, the well-defined backbone sequence of the macromolecule may be achieved by selection of the monomers used in the polymerization process (e.g., iterative functional exponential growth process). In some embodiments, the macromolecule may be regular. In other embodiments, the macromolecule may be irregular (e.g., block macromolecules, alternating macromolecules, periodic macromolecules).

In some embodiments, the glass transition temperature of the macromolecules may be greater than or equal to about −30° C., greater than or equal to about −15° C., greater than or equal to about 0° C., greater than or equal to about 15° C., greater than or equal to about 30° C., greater than or equal to about 45° C., greater than or equal to about 60° C., greater than or equal to about 75° C., or greater than or equal to about 90° C. In some instances, the glass transition temperature of macromolecules formed via iterative functional exponential growth may be less than or equal to about 120° C., less than or equal to about 100° C., less than or equal to about 80° C., less than or equal to about 60° C., less than or equal to about 40° C., less than or equal to about 20° C., less than or equal to about 0° C., or less than or equal to about −20° C. Combinations of the above-referenced ranges are also possible (e.g., greater than or equal to about 15° C. and less than or equal to about 80° C.). The glass transition temperature of the first component may be determined using differential scanning calorimetry (DSC), thermomechanical analysis (TMA), dynamic mechanical analysis (DMA), or may be obtained from a manufacturer's specifications. Unless indicated otherwise, the values of glass transition temperature described herein are determined by differential scanning calorimetry (DSC).

The macromolecules described herein may find use in a wide variety of applications. For example, the macromolecules described herein may find us in applications involving self-assembly, single-chain folding, biological display, drug-delivery, polyelectrolyte chemistry, and supported catalysis. The ability to specifically tune the functional groups and/or the end groups, to precisely control the molecules weight, to form a material comprising a macromolecule that is have no or low dispersity (e.g., dispersity index is approximately zero), and to control the stereochemistry of the macromolecule can allow for advantageous optimization of the macromolecules for use in these and other applications.

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Exemplary protecting groups are described in Protective Groups in Organic Synthesis, Third Ed. Greene, T. W.

and Wuts, P. G., Eds., John Wiley & Sons, New York: 1999, the entire contents of which are hereby incorporated by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p methoxybenzyloxymethyl (PMBM), (4methoxyphenoxy)methyl (pAOM), guaiacolmethyl (GUM), t-butoxymethyl, 4-pentenyloxymethyl (POM), siloxymethyl, 2-methoxyethoxymethyl (MEM), 2,2,2trichloroethoxymethyl, bis (2chloroethoxy)methyl, 2-(trimethylsilyl)ethoxymethyl (SEMOR), tetrahydropyranyl (THP), 3- bromotetrahydropyranyl, tetrahydrothiopyranyl, 1methoxycyclohexyl, 4-methoxytetrahydropyranyl (MTHP), 4-methoxytetrahydrothiopyranyl, 4-methoxytetrahydrothiopyranyl S,S-dioxide, 1[(2-chloro-4methyl)phenyl]-4-methoxypiperidin-4-yl (CTMP), 1,4-dioxan-2yl, tetrahydrofuranyl, tetrahydrothiofuranyl, 2,3,3a,4,5,6,7,7a-octahydro-7,8,8trimethyl-4,7methanobenzofuran-2yl, 1ethoxyethyl, 1-(2-chloroethoxy) ethyl, 1-methyl-1-methoxyethyl, 1-methylbenzyloxyethyl, 1-ethyl1b enzyloxy-2fluoroethyl, 2,2,2trichloroethyl, 2trimethylsilyl ethyl, 2-(phenylselenyl)ethyl, t-butyl, allyl, p-chlorophenyl, p-methoxyphenyl, 2,4dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4- (4'- bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4', 4"dimethoxyphenyl)methyl, 1,1-bis(4methoxyphenyl)-1'-pyrenylmethyl, 9anthryl, 9-(9-phenyl)xanthenyl, 9-(9phenyl-10oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyl diphenyl silyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxylnapththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4(1,1,3,3-tetramethylbutyl)phenoxyacetate, 2,4-bis (1,1dimethylpropyl)phenoxyacetate, chlorodiphenylacetate, isobutyrate, monosuccinoate, (E)-2- methyl-2-butenoate, o-(methoxyacyl)benzoate, α-naphthoate, nitrate, alkyl N,N, N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

The term "macromolecule" as used herein, refers to a molecule having a structure of which essentially comprises repeat units derived, actually or conceptually, from molecules of low relative molecular mass. A macromolecule may be a polymer or an oligomer.

The term "functionalizable group," as used herein, refers to a group or moiety which is capable of being chemically modified (e.g., via chemical reaction with a compound comprising a functional group). In some embodiments, the functionalizable group is a group or moiety which is capable of being chemically modified with a functional group via formation of a bond (e.g., covalent bond, non-covalent bond, etc.) or interaction (e.g., chemical or biological interaction) between the functionalizable group and the functional group. Functionalizable groups will be selected readily, by those of ordinary skill in the art, based upon the description provided herein and knowledge in the art.

The term "monomer" as used herein, has its ordinary meaning in the art and may refer to a molecule or a moiety on a molecule that is capable of participating in a reaction to become a part of the essential structure of a macromolecule.

The term "pendant group" as used herein, refers to a group attached to the backbone of a macromolecule that is neither oligomeric nor polymeric.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified sub stituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

Certain compounds of the present invention may exist in particular geometric or stereoisomeric forms. The present invention contemplates all such compounds, including cis- and trans-isomers, E- and Z-isomers, R- and S-enantiomers, diastereomers, (d)-isomers, (1)-isomers, (−)- and (+)-isomers, racemic mixtures thereof, and other mixtures thereof, as falling within the scope of the invention. Additional asymmetric carbon atoms may be present in a substituent such as an aliphatic (e.g., alkyl) or heteroaliphatic group. All such isomers, as well as mixtures thereof, are considered to be within this invention.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E.L. *Stereochemistry of Carbon Compounds* (McGrawHill, N.Y., 1962); and Wilen, S. H. *Tables of Resolving Agents and Optical Resolutions* p. 268 (E.L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straightchain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3pentanyl ($C_5$), amyl ($C_5$), neopentyl ($C_5$), 3methyl-2butanyl ($C_5$), tertiary amyl ($C_5$), and n-hexyl ($C_6$). Additional examples of alkyl groups include nheptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and for 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straightchain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-9}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2butenyl) or terminal (such as in 1-butenyl). Examples of C2_4 alkenyl groups include ethenyl (C2), 1propenyl ($C_3$), 2propenyl ($C_3$), 1butenyl ($C_4$), 2butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and for 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC2$_{2-10}$ alkenyl. In certain embodiments, the heteroalkenyl group is a substituted hetero$C_{2-10}$ alkenyl.

As used herein, "alkynyl" refers to a radical of a straightchain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("C2_9 alkynyl"). In some embodiments, an alkynyl group has 2 to 8 carbon atoms ("$C_{2-9}$ alkynyl"). In some embodiments, an alkynyl group has 2 to 7 carbon atoms ("$C_{2-8}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carboncarbon triple bonds can be internal (such as in 2butynyl) or terminal (such as in 1butynyl). Examples of $C_{2-4}$ alkynyl groups include, without limitation, ethynyl ($C_2$), 1-propynyl ($C_3$), 2propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and for 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

"Carbocyclyl," "carbocycle," or "carbocyclic" refers to a radical of a nonaromatic cyclic hydrocarbon group having from 3 to 10 ring carbon atoms ("$C_{3-10}$ carbocyclyl") and zero heteroatoms in the nonaromatic ring system. In some embodiments, a carbocyclyl group has 3 to 8 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged. or spiro ring system such as a bicyclic system ("bicyclic carbocyclyl"). Carbocyclylcan be saturated, and saturated carbocyclyl is referred to as "cycloalkyl." In some embodiments, carbocyclyl is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_5$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. Carbocyclyl can be partially unsaturated. Carbocyclyl including one or more C=C double bonds in the carbocyclic ring is referred to as "cycloalkenyl." Carbocyclyl including one or more CC triple bonds in the carbocyclic ring is referred to as "cycloalkynyl." Carbocyclyl includes aryl. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

As used herein, "heterocyclyl" or "heterocyclic" refers to a radical of a 3- to 14-membered nonaromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3membered heterocyclyl groups containing 1 heteroatom include, without limitation, azirdinyl, oxiranyl, and thiiranyl. Exemplary 4 membered heterocyclyl groups containing 1 heteroatom include, without limitation, azetidinyl, oxetanyl, and thietanyl. Exemplary 5 membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5 dione. Exemplary 5membered heterocyclyl groups containing 2 heteroatoms include, without limitation, dioxolanyl, oxathiolanyl and dithiolanyl. Exemplary 5 membered heterocyclyl groups containing 3 heteroatoms include, without limitation, triazolinyl, oxadiazolinyl, and thiadiazolinyl. Exemplary 6 membered heterocyclyl groups containing 1 heteroatom include, without limitation, piperidinyl, tetrahydropyranyl, dihydropyridinyl, and thianyl. Exemplary 6 membered heterocyclyl groups containing 2 heteroatoms include, without limitation, piperazinyl, morpholinyl, dithianyl, and dioxanyl. Exemplary 6membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl.

Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7dihydro-5H-furo[3,2-b]pyranyl, 5,7-dihydro-4H-thieno[2,3-c]pyranyl, 2,3-dihydro-1-H-pyrrolo[2,3-]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1naphthyl and 2naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6,10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2indolyl) or the ring that does not contain a heteroatom (e.g., 5indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6- membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond.

The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —50 O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, -OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{33}$, —P(=O)$_2$R$^{ee}$, —P(=O)(R$^{33}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkynyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroCi$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ roups; and each instance of Rgg is, independently, halogen, —CN, —$NO_2$, —$N_3$, —$SO_2H$, —$SO_3H$, —OH, —$Oc_{1-5}$ alkyl, —ON($C_{1-6}$ alkyl)$_2$, —N($C_{1-6}$ alkyl)$_2$, —N($C_{1-6}$ alkyl)$_3$$^+$X$^-$, —NH($C_{1-6}$ alkyl)$_2$$^+$X$^-$, —$NH_2$($C_{1-6}$ alkyl)$_2$, —N($C_{1-6}$ alkyl)$_3$ $^+$X$^-$, —NH($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$Co_2$($C_{1-6}$ Alkyl), —OC(=C)($C_{1-6}$ alkyl), —$OCO_2$($C_{1-6}$) alkyl, —C(=O)$NH_2$, —C(=O)N($C_{1-6}$ alkyl)$_2$, —OC(=O) NH($C_{1-6}$ alkyl), —NHC(=O)($C_{1-6}$ alkyl), —N($C_{1-6}$ alkyl) C(=O)($C_{1-6}$ alkyl), —$NHCO_2$($C_{1-6}$ alkyl), —NHC(=O)N ($C_{1-6}$ alkyl)$_2$, —NHC(=O)NH($C_{1-6}$ alkyl), —NHC(=O) $NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl)$_2$, —C(=NH)NH($C_{1-6}$ alkyl), —C(=NH)$NH_2$, —OC(=NH) N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(=NH)$NH_2$, —$NHSO_2$ ($C_{1-6}$ alkyl), —$SO_2$N($C_{1-6}$ alkyl)$_2$, —$SO_2$NH($C_{1-6}$ alkyl), —$SO_2$$NH_2$, —$SO_2$$C_{1-6}$ alkyl, —$SO_2$$OC_{1-6}$ alkyl, —$OSO_2$$C_{1-6}$ alkyl, —$SOC_{1-6}$ alkyl, —Si($C_{1-6}$ alkyl)$_3$, —OSi($C_{1-6}$ alkyl)$_3$—C(=S)N($C_{1-6}$ alkyl)$_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O) (O$C_{1-6}$ alkyl)$_2$, $C_{1-6}$ alkyl, $C_{1-6}$ perhaloalkyl, $C_{2-6}$ alkenyl, $C_{2-6}$ alkenyl, herteroC$_{1-6}$alkyl, heteroC$_{2-6}$alkenyl, hetero $C_{2-6}$alkynyl, $C_{3-10}$ carbocyclyl, $C_{6-10}$ aryl, 3-10 membered heteroaryl; or two geminal $R^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON (R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$) OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC (=O)SR$^{aa}$, —SC(=O)OR$_{aa}$, and —SC(=O)R$^{aa}$, wherein R$^{aa}$ and R$^{cc}$ are as defined herein.

As used herein, the term, "amino" refers to the group NH$_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), NHC(=O)R$^{aa}$, —NHCO$_2$R$^{aa}$, NHC(=O)N(R$^{bb}$)$_2$, —NHSO$_2$R$^{aa}$, —NHP (=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C (=O)N(R$^{bb}$)$_2$, —NR$^{bb}$(=NR$^{bb}$) N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$ X$^-$, wherein R$^{bb}$ and X$^-$are as defined herein.

As used herein, the term "sulfonyl" refers to a group selected from —SO$_2$N(R$^{bb}$)$_2$, —SO$_2$R$^{aa}$, —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "silyl" refers to the group —Si(R$^{aa}$)$_3$, wherein R$^{aa}$ is as defined herein.

The term "acyl" refers to a group having the general formula —C(=O)R$^{X1}$, —C(=O)OR$^{X1}$, —C(=O)—O—C (=O)R$^{X1}$, —C(=O)SR$^{X1}$, —C(=O)N(R$^{X1}$)$_2$, —C(=S) R$^{X1}$, —C(=S)N(R$^{X1}$)$_2$, and —C(=S)S(R$^{X1}$), —C(=NR$^{X1}$) R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di- aliphaticamino, mono- or di-heteroaliphaticamino, mono- or di- alkylamino, mono- or di- heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$$_2$, —CO$_2$R$^{aa}$, —C( C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, C$_{1-10}$ alkyl, C$_{1-10}$ perhaloalkyl, C$_{2-10}$ alkenyl, C$_{2-10}$ alkenyl, heteroC$_{1-10}$alkyl, herteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(r$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The invention is not intended to be limited in any manner by the above exemplary listing of substituents.

As used herein, the term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2hydroxyethanesulfonate, lactobionate, lactate, laurate, lauryl sulfate, malate, maleate, malonate, methanesulfonate, 2naphthalenesulfonate, nicotinate, nitrate, oleate, oxalate, palmitate, pamoate, pectinate, persulfate, 3phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-44}$ alkyl)$_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate. In some embodiments, the salt may be a pharmaceutically acceptable salt.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2hydroxy ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, ptoluenesulfonate, undecanoate, valerate salts, and the like. Pharmaceutically acceptable salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The following examples are intended to illustrate certain embodiments of the present invention, but do not exemplify the full scope of the invention.

EXAMPLES

Example 1

This example describes the synthesis of a precursor molecule and a monomer, as well as the click chemistry reaction between the molecules. Scheme 1 shows the synthetic method. The precursor molecule and monomer had an enantiomeric excess of at least 99.5%.

The monomer can be used to form a macromolecule having the structure:

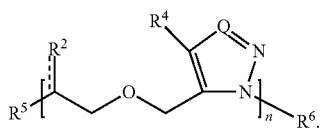

Synthesis of A2

Mg(ClO$_4$)$_2$ (981 mg, 4.4 mmol) was added to t-BuOH (19.6 g, 265 mmol) in a 500 mL round bottom flask (RBF). The mixture was stirred until the salt was totally dissolved. A1 (11.8 g, 44 mmol) was then added dropwise to the solution and the reaction was allowed to proceed for 3 days at room temperature. Afterwards, EtOAc was added and the solution was extracted 3 times with a 50% saturated brine solution. The organic layer was collected and dried under reduced pressure. THF (150 mL), PPh$_3$ (15.7 g, 60 mmol), and phthalimide (8.8 g, 60 mmol) were added to the crude liquid and stirred. DIAD (10.1 g, 50 mmol) was added dropwise to the solution and the reaction was left to react overnight. THF was removed under reduced pressure and EtOAc was added to the remaining material. The solution was extracted 3 times with distilled water and the organic layer was collected and concentrated under reduced pressure. Column chromatography was used to purify the desired product (16.0 g, 34 mmol). $^1$H NMR (300 MHz, CDCl$_3$, ppm): δH 7.85, 7.72, 4.75, 4.58, 4.49, 4.45 3.85, 1.08, 1.03.

Synthesis of A3

A2 (10 g, 21 mmol) was dissolved in THF (100 mL). Hydrazine hydrate (2.0 g, 40 mmol) was then added dropwise and the solution was left to react overnight. EtOAc was added to the solution and the solution was extracted 3 times with a 1% AcOH acqueous solution. The crude product was concentrated under reduced pressure. To the crude product was added MeOH (100 mL), CuSO$_4$-5H$_2$O (249 mg, 1 mmol), and K$_2$CO$_3$ (5.5 g, 40 mmol). 1H-Imidazole-1-sulfonyl azide-HCl salt (5.2 g, 25 mmol) was added protionwise to the solution and the reaction was left overnight at room temperature. EtOAc was added to the reaction and

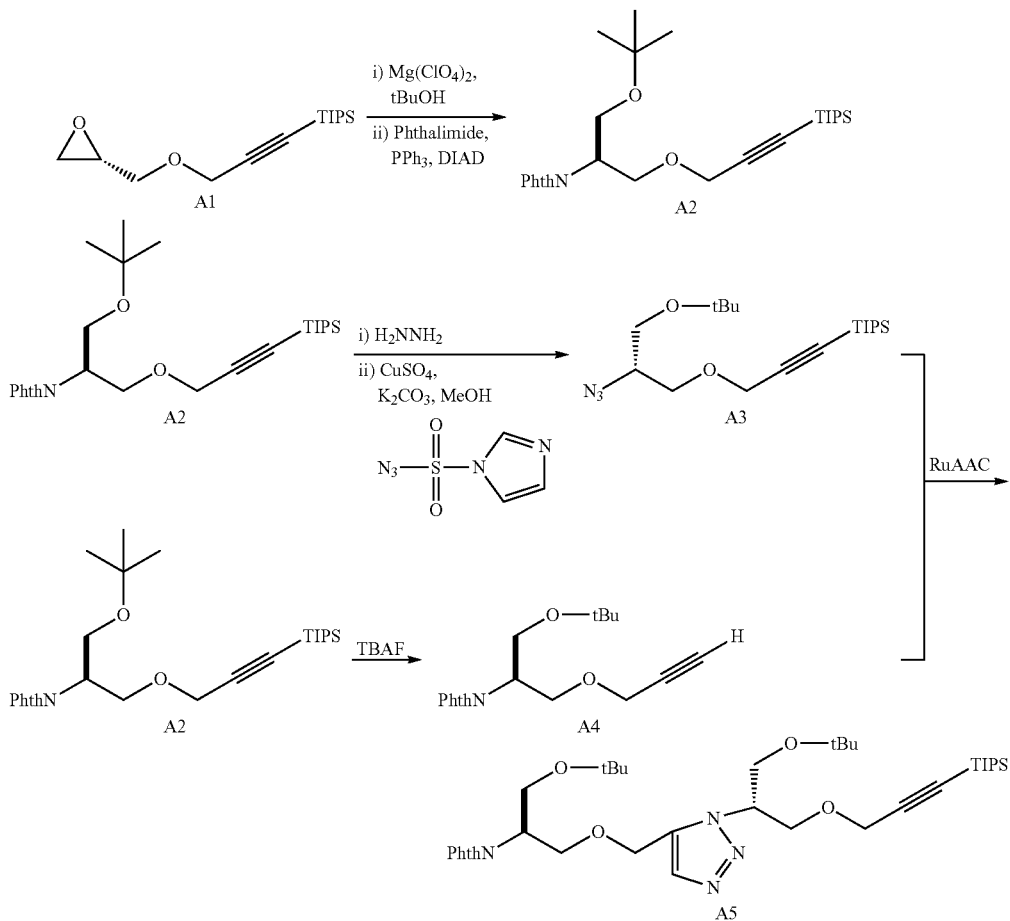

Scheme 1. Synthetic method.

the solution was then extracted 3 times with water. The crude product was concentrated under reduced pressure and was then purified by column chromatography to result in the desired product (6.2 g, 17 mmol). ¹H NMR (300 MHz, CDCl₃, ppm): δH 4.58, 4.47, 4.39, 3.85, 3.02, 1.07, 1.02.

Synthesis of A4

A2 (5.5 g, 11.6 mmol) was dissolved in THF (33 mL) in a 500 mL RBF. A 1M THF solution of TBAF (12.0 mL) was then added dropwise to the solution and left to react over 1 hour. EtOAc was added to the solution which was then extracted 3 times with water. The crude product A4 (3.46 g, 11 mmol) was concentrated under reduced pressure and used crude for further reactions. ¹H NMR (300 MHz, CDCl₃, ppm): δH 7.84, 7.73, 4.76, 4.57, 4.49, 3.83, 2.49, 1.08.

Synthesis of A5

1,4-Dioxane (2 mL) and Cp*RuCl(COD) (2.2 mg, 0.0057 mmol) were added to a mixture of A3 (100 mg, 0.27 mmol) and A4 (90 mg, 0.29 mmol). The reaction was stirred for 4 hours and then DCM was removed under reduced pressure. The crude reaction mixture was then purified by column chromatography resulting in A4 (150 mg, 0.22 mmol). ¹H NMR (400 MHz, CDCl₃, ppm): δH 7.85, 7.76, 7.56, 4.81, 4.76, 4.74, 4.59, 4.48, 3.82, 3.65, 1.10, 1.08, 1.02.

Example 2

This example describes the synthesis of a precursor molecule and a monomer, as well as the click chemistry reaction between the molecules. Scheme 2 shows the synthetic method. The precursor molecule and monomer had an enantiomeric excess of at least 99.5%.

The monomer can be used to form a macromolecule having the structure:

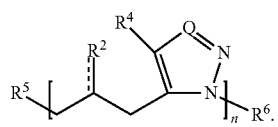

Scheme 2. Synthetic method.

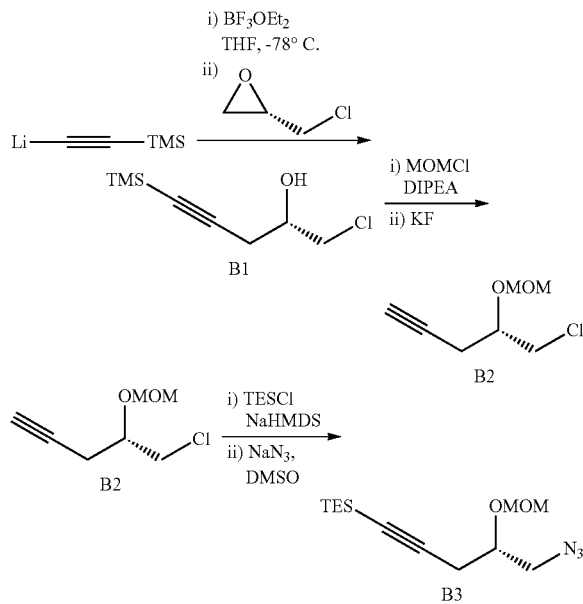

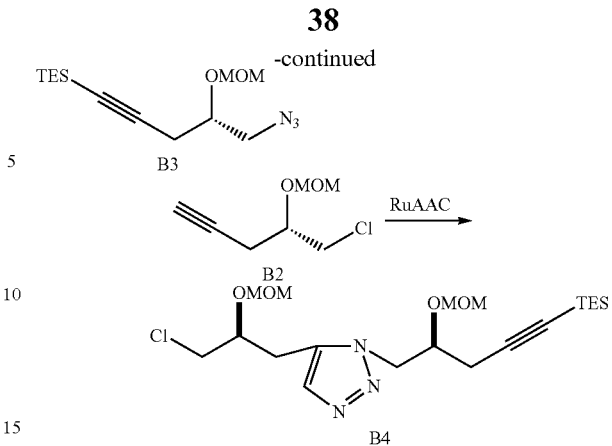

Synthesis of B1

Ethynyltrimethylsilane (53.0 g, 540 mmol), was added to anhydrous THF (540 mL) in a dry 1000 mL RBF. The solution was cooled to −78° C. and a 2.5M Hexanes solution of n-BuLi (216 mL) was added dropwise to the solution. The reaction was left at −78° C. for 15 minutes before BF₃ etherate (76.64 g, 540 mmol) was added to it dropwise. After another 15 minutes, (S)-Epichlorohydrin (25 g, 270 mmol) was added dropwise the the solution. The reaction was left at −78° C. for 2 hours and allowed to warm to 0° C. and reacted a further 2 hours. AcOH (25 mL) was added to quench the reaction. EtOAc was then added and the solution was extracted 3 times with water. The crude product B1 (44.4 g, 233 mmol) was concentrated under reduced pressure and used without further purification. ¹NMR (300 MHz, CDCl₃, ppm): δH 3.93, 3.73, 3.64, 2.46, 2.41, 0.15.

Synthesis of B2

CHCl₃ (120 mL) and DIPEA (59 g, 460 mmol) was added to B1 (44 g, 231 mmol)) in a 500 mL RBF. MOMCl (37.0 g, 460 mmol) was then added dropwise to the solution and it was left to react for 36 hours at 35° C. Water was then added to quench the reaction and the organic phase was extracted 3 times with water. The organic layer was concentrated under reduced pressure and the resulting product was used without further purification. MeOH (400 mL) and KF (58 g, 1 mol) were added to the product and the resulting solution was heated to 45° C. and left to react for 4 hours. MeOH was then removed under reduced pressure and EtOAc was added. The organic solution was extracted 3 times with water and then concentrated under reduced pressure. The crude product was then purified by column chromatography to result in B2 (27.2 g, 168 mmol). ¹H NMR (300 MHz, CDCl₃, ppm): δH 4.76, 3.98, 3.75, 3.67, 3.45, 2.51, 2.47, 1.98.

Synthesis of B3

B2 (15.0 g, 93 mmol) was added to anhydrous THF (300 mL) in a dry 1000 mL RBF. The solution was cooled to −78° C. and a 2M solution of NaHMDS (50 mL) was added dropwise. After 15 minutes, TESCl (18.1 g, 120 mmol) was added dropwise and the solution was then allowed to warm to room temperature. AcOH (15 mL) was added dropwise to quench the reaction and THF was then removed under reduced pressure. EtOAc was added and the solution was extracted 3 times with water. The organic layer was then concentrated under reduced pressure and the crude product was used without further purification. To the crude product was added DMSO (500 mL) and NaN₃ (19.5 g, 300 mmol) and heated to 45° C. After 2 days, EtOAc was added to the reaction mixture and extracted 3 times with a 2% w/w LiCl aqueous solution. EtOAc was removed under reduced pressure and the crude product was purified by column chromatography resulting in B3 (17.5 g, 62 mmol). $^1$H NMR (300 MHz, CDCl$_3$, ppm): δH 4.76, 3.89, 3.35, 3.33, 3.29, 2.48, 2.42, 0.98, 0.15.

Synthesis of B4

1,4-Dioxane (2 mL) and Cp*RuCl(COD) (2.5 mg, 0.0064 mmol) were added to a mixture of B2 (50 mg, 0.31 mmol) and B3 (90 mg, 0.32 mmol). The reaction was stirred for 4 hours and then DCM was removed under reduced pressure. The crude reaction mixture was then purified by column chromatography resulting in B4 (112 mg, 0.25 mmol). $^1$H NMR (400 MHz, CDCl$_3$, ppm): δH 7.40, 5.15, 4.99, 4.89, 4.87, 3.57, 3.45, 3.38, 3.28, 2.55, 2.51, 0.95, 0.55.

Example 3

This example describes the synthesis of a precursor molecule and a monomer, as well as the click chemistry reaction between the molecules. Scheme 3 shows the synthetic method. The precursor molecule and monomer had an enantiomeric excess of at least 99.5%.

The monomer can be used to form a macromolecule having the structure:

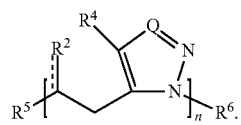

Scheme 3. Synthetic method.

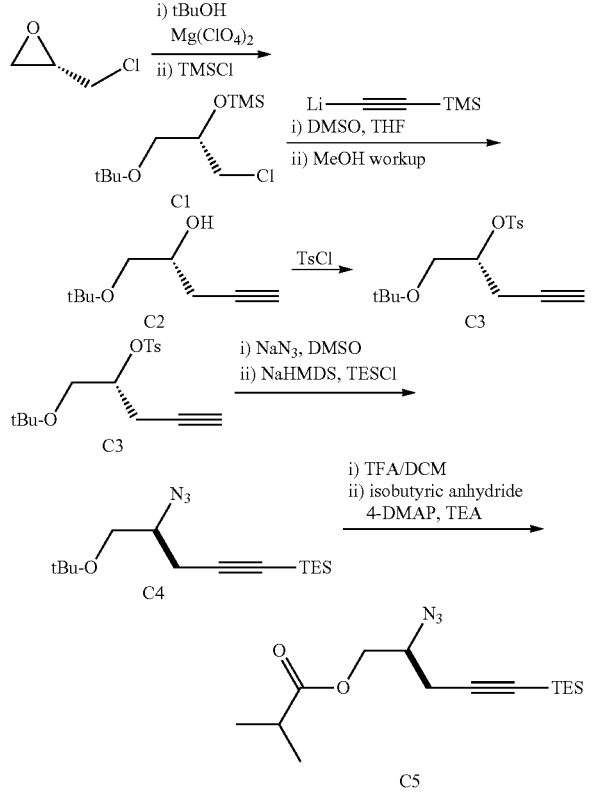

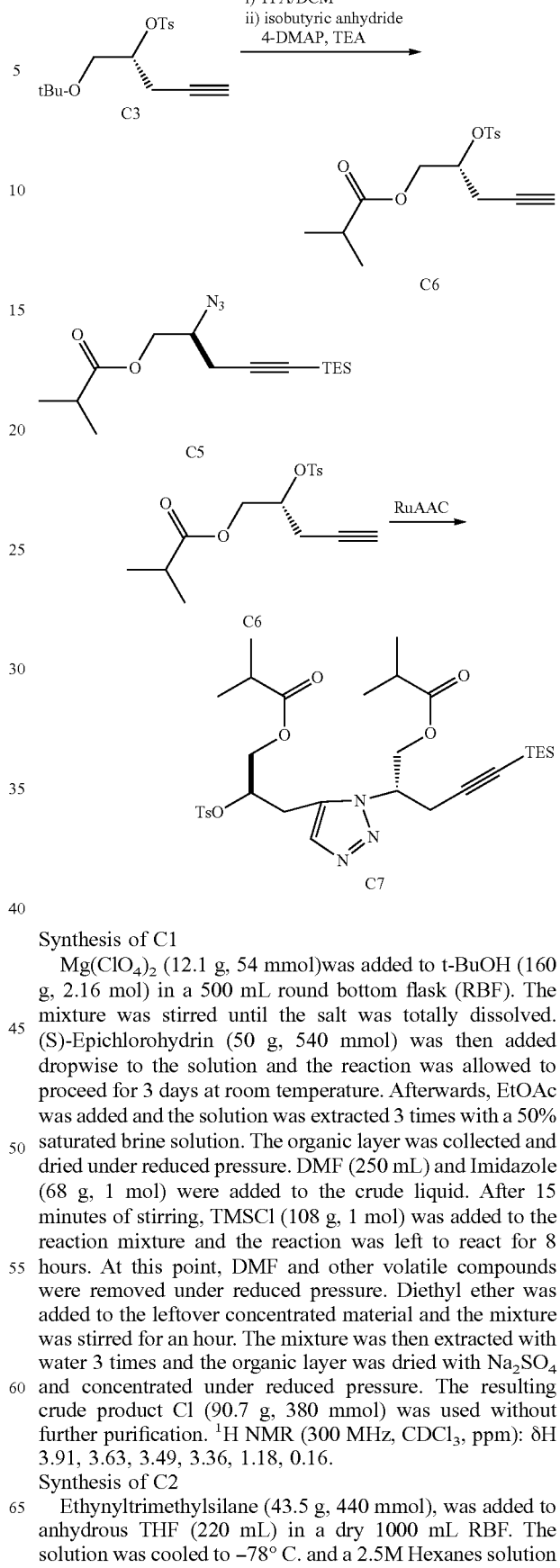

Synthesis of C1

Mg(ClO$_4$)$_2$ (12.1 g, 54 mmol) was added to t-BuOH (160 g, 2.16 mol) in a 500 mL round bottom flask (RBF). The mixture was stirred until the salt was totally dissolved. (S)-Epichlorohydrin (50 g, 540 mmol) was then added dropwise to the solution and the reaction was allowed to proceed for 3 days at room temperature. Afterwards, EtOAc was added and the solution was extracted 3 times with a 50% saturated brine solution. The organic layer was collected and dried under reduced pressure. DMF (250 mL) and Imidazole (68 g, 1 mol) were added to the crude liquid. After 15 minutes of stirring, TMSCl (108 g, 1 mol) was added to the reaction mixture and the reaction was left to react for 8 hours. At this point, DMF and other volatile compounds were removed under reduced pressure. Diethyl ether was added to the leftover concentrated material and the mixture was stirred for an hour. The mixture was then extracted with water 3 times and the organic layer was dried with Na$_2$SO$_4$ and concentrated under reduced pressure. The resulting crude product C1 (90.7 g, 380 mmol) was used without further purification. $^1$H NMR (300 MHz, CDCl$_3$, ppm): δH 3.91, 3.63, 3.49, 3.36, 1.18, 0.16.

Synthesis of C2

Ethynyltrimethylsilane (43.5 g, 440 mmol), was added to anhydrous THF (220 mL) in a dry 1000 mL RBF. The solution was cooled to −78° C. and a 2.5M Hexanes solution of n-BuLi (176 mL) was added dropwise to the solution. The reaction was left at −78° C. for 15 minutes before the reaction mixture was allowed to warm to room temperature. C1 (50 g, 209 mmol) and DMSO (150 mL) were then added to the solution. After four hours of reaction, MeOH (40 mL) was added dropwise to quench the reaction. The product was concentrated under reduced pressure and then EtOAc was added and the resulting solution was extracted 3 times with water. The organic layer was dried with $Na_2SO_4$ and then concentrated under reduced pressure to yield product C2 (23.1 g, 152 mmol), which was used without further purification. $^1$HNMR (300 MHz, $CDCl_3$, ppm): δH 3.88, 3.50, 3.38, 3.36, 2.53, 2.49, 1.96 1.21.

Synthesis of C3

DCM (300 mL), 4-DMAP (23.2 g, 190 mmol), and TEA (22.1 g, 219 mmol) were added to C3 (22 g, 146 mmol) and stirred together until homogenous. Tosyl chloride (27.8 g, 146 mmol) was then added portionwise and the reaction was left to react overnight. Water was added and the solution was extracted 1 time with water and 2 times with 1% AcOH. The organic layer was isolated and dried with $Na_2SO_4$ and then concentrated under reduced pressure to yield C3 (48.4 g, 136 mmol). $^1$H NMR (300 MHz, $CDCl_3$, ppm): δH 7.83, 7.37, 4.59, 3.54, 3.52, 2.61, 2.46, 2.35, 1.99.

Synthesis of C4

DMSO (450 mL) and $NaN_3$ (20.1 g, 309 mmol) were added to C3 (32 g, 103 mmol), and the resulting solution was heated to 50° C. and left to react for 24 hours. EtOAc was added and the solution was extracted 3 times with 1% w/w LiCl acqueous solution. The organic phase was isolated, dried with $Na_2SO_4$, and concentrated under reduced pressure. The crude material was then purified by column chromatography to yield a clear oil. Anhydrous THF (400 mL) was added to this oil and the solution was cooled to −78° C. 2M NaHMDS in THF (30 mL) was added dropwise to the solution, and after 15 minutes TESCl (10.6 g, 70 mmol) was added dropwise to the solution. After another 15 minutes the reaction was warmed to room temperature and AcOH (10 mL) was added to quench the reaction. The reaction mixture was concentrated under reduced pressure and then EtOAc was added. The solution was extracted with 3 times with water and the organic layer was isolated, dried with $Na_2SO_4$, and concentrated. The product was purified by column chromatography to yield $C_4$ as a clear oil (15.7 g, 53 mmol). $^1$H NMR (300 MHz, $CDCl_3$, ppm): 41 7.84, 3.91, 3.63, 3.49, 3.36, 1.18, 0.16.

Synthesis of C5

A 1:1 mixture of TFA and DCM (200 mL) was added to C4 (15 g, 50.8 mmol) and reacted at 35° C. for 1 hour. TFA and DCM were removed by reduced pressure and the product was purified by column chromatography. The purified product was then added to a solution of DCM (150 mL), 4-DMAP (2.44 g, 20 mmol), and TEA (6.06 g, 60 mmol). Isobutyric anhydride (7.9 g, 50 mmol) was then added and left to react for 15 minutes.

Volatile compounds were removed under reduced pressure and the desired product C5 (11.4 g, 37 mmol) was isolated by column chromatography. $^1$H NMR (300 MHz, $CDCl_3$, ppm): δH 4.32, 4.18, 3.79, 2.63, 2.60, 1.22, 1.01, 0.60.

Synthesis of C6

A 1:1 mixture of TFA and DCM (200 mL) was added to C3 (16 g, 52 mmol) and reacted at 35° C. for 1 hour. TFA and DCM were removed by reduced pressure and the product was purified by column chromatography. The purified product was then added to a solution of DCM (150 mL), 4-DMAP (2.44 g, 20 mmol), and TEA (6.06 g, 60 mmol).

Isobutyric anhydride (7.9 g, 50 mmol) was then added and left to react for 15 minutes. Volatile compounds were removed under reduced pressure and the desired product C6 (13.6 g, 42 mmol) was isolated by column chromatography. $^1$H NMR (300 MHz, $CDCl_3$, ppm): 41 7.83, 7.37, 4.79, 4.30, 4.22, 2.63, 2.48, 2.46, 2.01, 1.14.

Synthesis of C7

1,4-Dioxane (1 mL) and Cp*RuCl(COD) (1.2 mg, 0.0031 mmol) were added to a mixture of C5 (50 mg, 0.16 mmol) and C6 (50 mg, 0.15 mmol). The reaction was stirred for 4 hours and then DCM was removed under reduced pressure. The crude reaction mixture was then purified by column chromatography resulting in C7 (82 mg, 0.13 mmol). $^1$H NMR (400 MHz, $CDCl_3$, ppm):7.78, 7.58, 7.26, 4.90, 4.80, 4.65, 4.20, 4.01, 3.12, 2.89, 2.57, 2.44, 2.29, 1.09, 0.95, 0.56.

EXAMPLE 4

This example describes the synthesis of a precursor molecule and a monomer, as well as the click chemistry reaction between the molecules. Scheme 4 shows the synthetic method. The precursor molecule and monomer had an enantiomeric excess of at least 99.5%.

The monomer can be used to form a macromolecule having the structure:

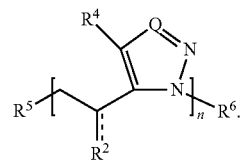

Scheme 4. Synthesis method.

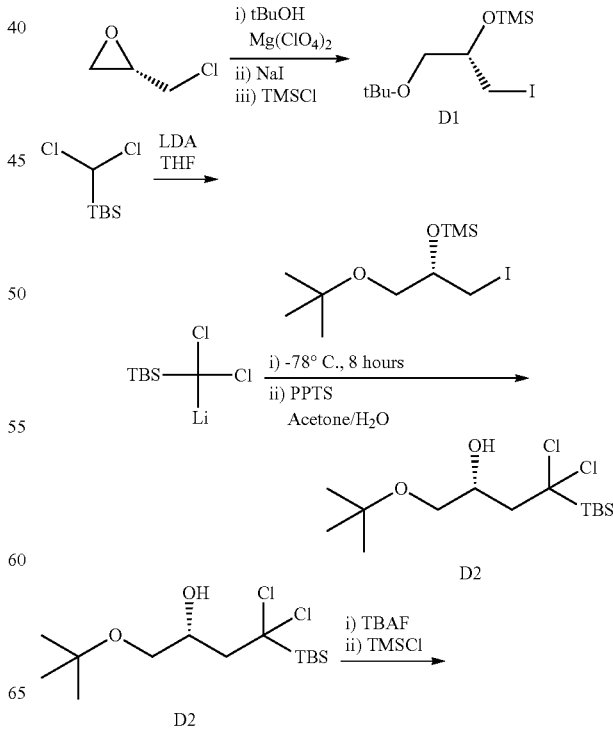

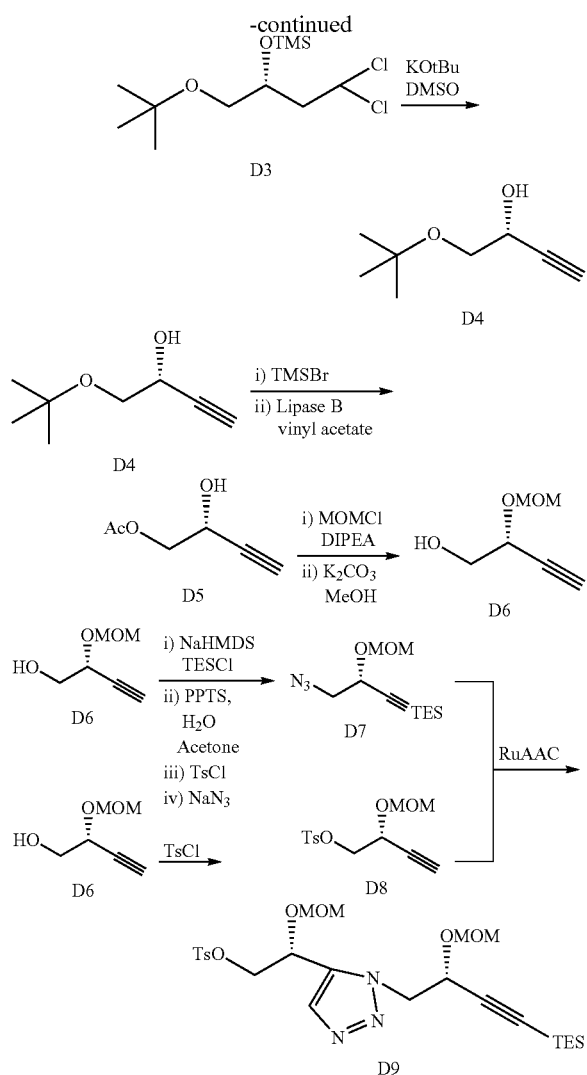

Synthesis of D1

Mg(ClO$_4$)$_2$ (12.1 g, 54 mmol) was added to t-BuOH (160 g, 2.16 mol) in a 500 mL round bottom flask (RBF). The mixture was stirred until the salt was totally dissolved. (S)-Epichlorohydrin (50 g, 540 mmol) was then added dropwise to the solution and the reaction was allowed to proceed for 3 days at room temperature. Afterwards, EtOAc was added and the solution was extracted 3 times with a 50% saturated brine solution. The organic layer was collected and dried under reduced pressure. DMF (250 mL) and NaI (223 g, 1.5 mol) were added to the crude liquid, and this reaction mixture was heated to 100° C. for 2 hours. EtOAc was added to the solution, which was then extracted 3 times with water. The organic layer was then isolated, dried with Na$_2$SO$_4$, and concentrated under reduced pressure. The crude liquid was used without further purification in the next step. DMF (200 mL) and Imidazole (68 g, 1 mol) were added to the crude liquid. After 15 minutes of stirring, TMSCl (108 g, 1 mol) was added to the reaction mixture and the reaction was left to react for 8 hours. At this point, DMF and other volatile compounds were removed under reduced pressure. Diethyl ether was added to the leftover concentrated material and the mixture was stirred for an hour. The mixture was then extracted with water 3 times and the organic layer was dried with Na$_2$SO$_4$ and concentrated under reduced pressure. The resulting crude product D1 (134 g, 400 mmol) was used without further purification. $^1$H NMR (300 MHz, CDCl$_3$, ppm): δH 3.79, 3.56, 3.33, 3.28, 0.19.

Synthesis of D2 t-Butyl(dichloromethyl)dimethylsilane (82 g, 410 mmol) was added to anhydrous THF (1.2 L) in a dry RBF. The solution was cooled to −78° C. and 2M LDA in THF (205 mL) was added dropwise. After 1 hour, the solution was kept at −78° C. and D1 (66.4 g, 200 mmol) was added dropwise to the solution. The reaction was left at −78° C. for 8 hours at which point the reaction was quenched with water. EtOAc was added and the solution was extracted 3 times with water. The organic layer was dried with Na$_2$SO$_4$ and concentrated under reduced pressure. The crude product D2 (55.3 g, 166 mmol, contaminated with starting material and evaluated by NMR) was used without further purification. $^1$H NMR (300 MHz, CDCl$_3$, ppm): 61-1 4.63, 3.75, 3.67, 3.33, 2.59, 2.36, 1.05, 1.01, 0.25.

Synthesis of D3

D2 (50 g, 150 mmol) was dissolved in THF (450 mL) and 1M TBAF in THF (450 mL) was added dropwise to the solution. After 15 minutes, EtOAc was added and the solution was extracted 3 times with water. The organic layer was dried with Na2SO4 and concentrated under reduced pressure. DMF (50 mL) and imidazole (13.6 g, 200 mmol) were then added to the resulting crude liquid. TMSCl (22 g, 200 mmol) was then added and the reaction was left at room temperature for 8 hours, and then DMF and other volatiles were removed under reduced pressure. Diethyl ether was added and the mixture was stirred for 1 hour. The solution was then extracted 3 times with water, the organic layer was dried with Na$_2$SO$_4$, and the crude product was concentrated under reduced pressure to yield D3 (26.1 g, 89 mmol) which was used without further purification. $^1$ H NMR (300 MHz, CDCl$_3$, ppm): δH 5.80, 4.08, 3.49, 3.42, 2.48, 2.43, 0.89.

Synthesis of D4

DMSO (480 mL) was added to D3 (23.5 g, 80 mmol) and the mixture was stirred until homogenous. KOtBu (26.9 g, 240 mmol) was then added to the solution and the reaction was left at room temperature for 2 hours. EtOAc was added to the solution, which was then extracted 3 times with water. The organic layer was isolated, dried with Na$_2$SO$_4$, and concentrated under reduced pressure. The resulting oil was purified with column chromatography to yield D4 (6.4 g, 45 mmol). $^1$H NMR (300 MHz, CDCl$_3$, ppm): δH 4.46, 3.54, 3.45, 2.63, 2.45, 1.22.

Synthesis of D5

D4 (3.0 g, 20.8 mmol) was dissolved in Acetonitrile (50 mL), and TMSBr (6.12 g, 40 mmol) was then added to the solution. After 1 hour, 1% AcOH in water (10 mL) was added and all volatiles were removed under reduced pressure. Acetonitrile (20 mL), vinyl acetate (20 mL), and lipase B (250 mg) were then added and the reaction was left over night to react. Volatile compounds were removed under reduced pressure and the crude mixture was purified by column chromatography to yield D5 (1.98 g, 14.3 mmol) as a clear liquid. $^1$H NMR (300 MHz, CDCl$_3$, ppm): δH 4.86, 4.69, 4.30, 2.63, 2.13.

Synthesis of D6

CHCl$_3$ (20 mL) and DIPEA (3.53 g, 27.4 mmol) was added to D5 (1.9 g, 13.7 mmol) in a 500 mL RBF. MOMCl (2.21 g, 27.4 mmol) was then added dropwise to the solution and it was left to react for 36 hours at 35 ° C. Water was then added to quench the reaction and the organic phase was extracted 3 times with water. The organic layer was dried with Na$_2$SO$_4$ and concentrated under reduced pressure. MeOH (30 mL) and K$_2$CO$_3$ (4.15 g, 30 mmol) were then added to the resulting oil and the mixture was heated to 45° C. for 1 hour. MeOH was then removed under reduced pressure, EtOAc was added and the solution was extracted 3 times with water. The organic layer was isolated, dried with Na$_2$SO$_4$, and concentrated under reduced pressure. This crude mixture was purified with column chromatography resulting in D6 (1.42 g, 10 mmol). $^1$H NMR (300 MHz, CDCl$_3$, ppm): δH 4.98, 4.84, 3.58, 3.47, 3.40, 2.71.

Synthesis of D7

D6 (1.0 g, 7.0 mmol) was added to anhydrous THF (50 mL) in a dry RBF. The solution was cooled to −78° C. and 2M NaHMDS in THF (7.2 mL) was added dropwise. After 15 minutes, TESCl (2.71 g, 18 mmol) was added dropwise and after 1 hour, the reaction was allowed to warm up to room temperature. AcOH (7 mL) was added to quench the reaction. EtOAc was added and the solution was extracted 3 times with water. The organic layer was dried with Na$_2$SO$_4$ and concentrated under reduced pressure. A 9:1 mixture of Acetone/H$_2$O (20 mL) and PPTS (251 mg, 1 mmol) added. The reaction was heated to 60° C. for 4 hours. Acetone was removed under reduced pressure and EtOAc was added and the solution was extracted 3 times with water. The organic layer was dried with Na$_2$SO$_4$ and concentrated under reduced pressure. DCM (20 mL), 4-DMAP (366 mg, 3.0 mmol), and TEA (1.0 g, 10 mmol) was then added and the mixture was stirred until homogenous. Tosyl chloride (1.52g, 8 mmol) was then added and the reaction was left to react overnight. DCM was removed under reduced pressure and EtOAc was added and the solution was extracted 1 time with water and 2 times with 1% AcOH in water. The organic layer was dried with Na$_2$SO4 and concentrated under reduced pressure. DMSO (28 mL) and NaN$_3$ (910 mg, 14 mmol) were then added and the solution was heated to 45° C. for 24 hours, after which EtOAc was added. The solution was extracted 3 times with water. The organic layer was dried with Na$_2$SO$_4$ and concentrated under reduced pressure. The resulting liquid was then purified by column chromatography to yield D7 (1.16 g, 4.1 mmol). $^1$H NMR (300 MHz, CDCl$_3$, ppm): δH 4.98, 4.84, 3.39, 3.30, 3.25, 1.05, 0.15.

Synthesis of D8

DCM (10 mL), 4-DMAP (122 mg, 1 mmol), and TEA (400 mg, 4 mmol) was added to D6 (400 mg, 2.8 mmol) and the mixture was stirred until homogenous. Tosyl chloride (572 mg, 3.0 mmol) was then added and the reaction was left to react overnight. DCM was removed under reduced pressure and EtOAc was added and the solution was extracted 1 time with water and 2 times with 1% AcOH in water. The organic layer was dried with Na$_2$SO$_4$ and concentrated under reduced pressure leaving the product D8 (810 mg, 2.7 mmol) which ws used without further purification. $^1$H NMR (300 MHz, CDCl$_3$, ppm): 61-1 7.83, 7.30, 4.98, 4.91, 3.92, 3.78, 3.42, 2.71, 2.55.

Synthesis of D9

1,4-dioxane (1 mL) and Cp*RuCl(COD) (1.4 mg, 0.0036 mmol) were added to a mixture of D7 (50 mg, 0.18 mmol) and D8 (50 mg, 0.17 mmol). The reaction was stirred for 4 hours and then DCM was removed under reduced pressure. The crude reaction mixture was then purified by column chromatography resulting in D9 (89 mg, 0.15 mmol). $^1$H NMR (400 MHz, CDCl$_3$, ppm): 61-1 7.89, 7.60, 7.25, 5.30, 5.11, 4.97, 4.84, 3.92, 3.84, 3.73, 3.50, 3.41, 1.07, 0.18.

Example 5

This example describes the synthesis of a precursor molecule and a monomer, as well as the click chemistry reaction between the molecules. Scheme 3 shows the synthetic method. The precursor molecule and monomer had an enantiomeric excess of at least 99.5%.

The monomer can be used to form a macromolecule having the structure:

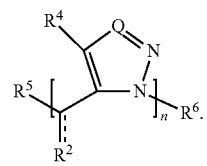

Scheme 5. Synthetic method.

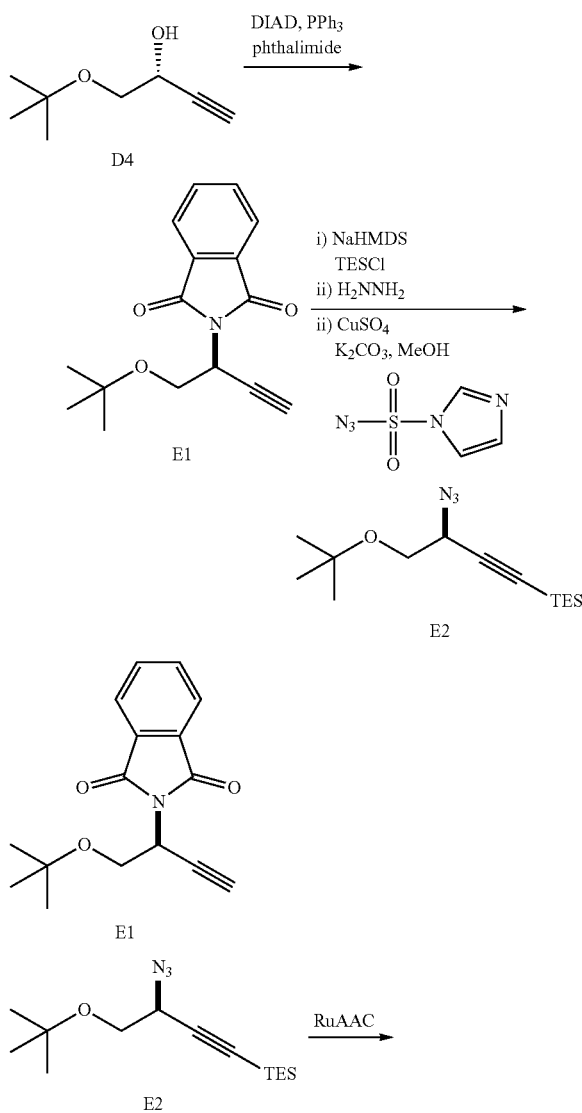

-continued

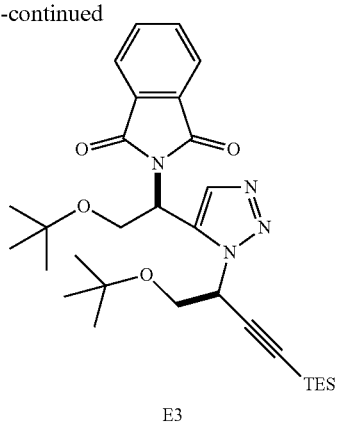

E3

Synthesis of E1

THF (30 mL), PPh$_3$ (1.05 g, 4 mmol), and phthalimide (559 mg, 3.8 mmol) were added to D4 (540 mmol, 3.3 mmol) and stirred. DIAD (728 mg, 3.6 mmol) was added dropwise to the solution and the reaction was left to react overnight. THF was removed under reduced pressure and EtOAc was added to the remaining material. The solution was extracted 3 times with distilled water and the organic layer was collected and concentrated under reduced pressure. Column chromatography was used to purify the desired product E1 (823 mg, 3.0 mmol). [1] HNMR (300 MHz, CDCl$_3$, ppm): δH 7.85, 7.72, 5.16, 4.31, 4.23, 2.39, 1.09.

Synthesis of E2

E1 (325 mg, 1.3 mmol) was added to anhydrous THF (10 mL) in a dry RBF. The solution was cooled to −78° C. and 2M NaHMDS in THF (0.7 mL) was added dropwise. After 15 minutes, TESCl (226 mg, 1.5 mmol) was added dropwise and after 1 hour, the reaction was allowed to warm up to room temperature. AcOH (1 mL) was added to quench the reaction. EtOAc was added and the solution was extracted 3 times with water. The organic layer was dried with Na$_2$SO$_4$ and concentrated under reduced pressure. THF (10 mL) and Hydrazine hydrate (75 mg, 1.5 mmol) were then added and left to react for 1 hour at room temperature. EtOAc was added and the solution was extracted 3 times with saturated bicarbonate solution. To the crude product was added MeOH (10 mL), CuSO4-5H$_2$O (12 mg, 0.05 mmol), and K$_2$CO$_3$ (249 mg, 1.8 mmol). 1H-Imidazole-1-sulfonyl azide-HCl salt (219 mg, 1.05 mmol) was added protionwise to the solution and the reaction was left overnight at room temperature. EtOAc was added to the reaction and the solution was then extracted 3 times with water. The crude product was concentrated under reduced pressure and was then purified by column chromatography to result in the desired product E2 (307 mg, 0.95 mmol). $^1$H NMR (300 MHz, CDCl$_3$, ppm): 41 4.35, 4.28, 4.12, 1.12, 1.06.

Synthesis of E3

1,4-dioxane (1 mL) and Cp*RuCl(COD) (0.81 mg, 0.0021 mmol), were added to a mixture of E1 (29 mg, 0.11 mmol) and E2 (30 mg, 0.11 mmol). The reaction was stirred for 4 hours and then DCM was removed under reduced pressure. The crude reaction mixture was then purified by column chromatography resulting in E3 (48 mg, 0.081 mmol). $^1$H NMR (400 MHz, CDCl$_3$, ppm): 41 7.86, 7.74, 7.44, 5.61, 5.25, 4.40, 4.35, 4.25, 1.12, 1.09, 1.04.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claiemd is:

1. A compound comprising Formula (I):

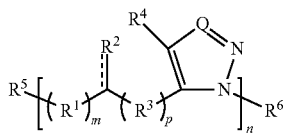

or a salt thereof, wherein:
each Q is independently N or $N^+(R^\#)$
each $R^1$ and $R^3$ is independently O, S, optionally substituted amino, optionally substituted acylene, optionally substituted alkylene, optionally substituted carbocyclylene, optionally substituted heteroalkylene, optionally substituted heterocyclylene, optionally substituted arylene, or optionally substituted heteroarylene;
each $R^2$ is independently O, $OR^\#$, S, $SR^{190}$ $N(R^\#)$, $N(R^\#)_2$, $C(R^*)_2$, $C(R^*)_3$, $C(=O)R^*$, $C(=NR^\#)R^*$, or $C(=S)R^*$;
each ===== is independently a single or double bond, provided that when ===== is a double bond each $R^2$ is independently O, S, $N(R^\#)$, or $C(R^*)_2$, and when ===== is a single bond each $R^2$ is independently $OR^\#$, $SR^\#$, $N(R^\#)_2$, $C(R^*)_3$, $C(=O)R^*$, $C(=NR^\#)R^*$, or $C(=S)R^*$;
each $R^4$ is independently hydrogen, halo, optionally substituted alkyl, optionally substituted carbocyclyl, optionally substituted heteroalkyl, optionally substituted heterocyclyl, optionally substituted aryl, optionally substituted heteroaryl, or a metal;
$R^5$ is azide, hydroxyl, optionally substituted amino, optionally substituted thiol, optionally substituted acyl, optionally substituted alkyl, optionally substituted carbocyclyl, optionally substituted heteroalkyl, optionally substituted heterocyclyl, optionally substituted alkenyl, optionally substituted heteroalkenyl, optionally substituted aryl, optionally substituted heteroaryl, or an electrophile;
$R^6$ is optionally substituted alkyl, optionally substituted carbocyclyl, optionally substituted heteroalkyl, optionally substituted heterocyclyl, optionally substituted alkenyl, optionally substituted heteroalkenyl, optionally substituted alkynyl, optionally substituted heteroalkynyl, optionally substituted aryl, or optionally substituted heteroaryl;
each $R^\#$ is independently hydrogen, optionally substituted alkyl, optionally substituted carbocyclyl, optionally substituted heteroalkyl, optionally substituted heterocyclyl, optionally substituted alkenyl, optionally substituted heteroalkenyl, optionally substituted aryl, optionally substituted heteroaryl, optionally substituted silyl, or optionally substituted sulfonyl; and
each $R^*$ is independently hydrogen, halo, hydroxyl, optionally substituted amino, optionally substituted thiol, optionally substituted acyl, optionally substituted alkyl, optionally substituted carbocyclyl, optionally substituted heteroalkyl, optionally substituted heterocyclyl, optionally substituted alkenyl, optionally substituted heteroalkenyl, optionally substituted aryl, or optionally substituted heteroaryl;
each m and p is independently 0, 1, 2, 3, 4, 5, 6, 7, 8, 9, or 10; and
n is an integer between 8 and 500.

2. The compound of claim 1, wherein each ===== is independently a single bond.

3. The compound of claim 1, wherein each $R^1$ and $R^3$ is independently O, S, optionally substituted amino, optionally substituted alkylene, or optionally substituted heteroalkylene.

4. The compound of claim 1, wherein each $R^1$ and $R^3$ is independently O, optionally substituted amino, or optionally substituted alkylene.

5. The compound of claim 1, wherein each m and p is independently 0, 1, 2, 3, 4, or 5.

6. The compound of claim 1, wherein each m is independently 0 or 1.

7. The compound of claim 1, wherein Formula (I) has the structure:

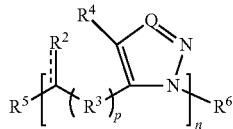

or a salt thereof.

8. The compound of claim 1, wherein Formula (I) has the structure:

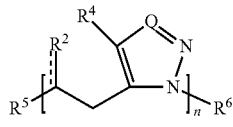

or a salt thereof.

9. The compound of claim 1, wherein Formula (I) has the structure:

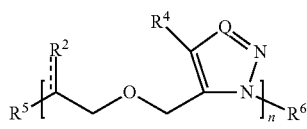

or a salt thereof.

10. The compound of claim 1, wherein Formula (I) has the structure:

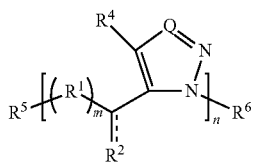

or a salt thereof.

11. The compound of claim 1, wherein Formula (I) has the structure:

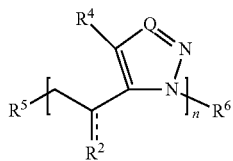

or a salt thereof.

12. The compound of claim 1, wherein Formula (I) has the structure:

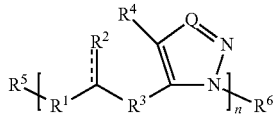

or a salt thereof.

13. The compound of claim 1, wherein Formula (I) has the structure:

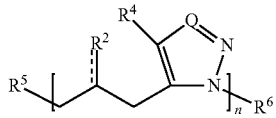

or a salt thereof.

14. The compound of claim Jany preceding claim, wherein Formula (I) has the structure:

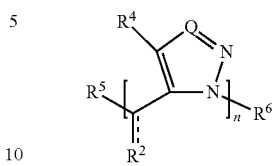

or a salt thereof.

15. The compound of claim 1, wherein at least one $R^2$ is $C(R^*)_3$ and wherein the at least one $C(R^*)_3$ has the structure:

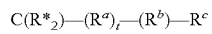

$$C(R^*_2)-(R^a)_t-(R^b)-R^c$$

wherein:
each $R^a$ is independently optionally substituted alkylene, optionally substituted alkenylene, or optionally substituted alkynylene;

$R^b$ is O, N(R), or S;

$R^c$ is hydrogen, optionally substituted acyl, optionally substituted alkyl, optionally substituted carbocyclyl, optionally substituted heteroalkyl, optionally substituted alkenyl, optionally substituted heteroalkenyl, optionally substituted alkynyl, optionally substituted heteroalkynyl, optionally substituted heterocyclyl, optionally substituted aryl, optionally substituted heteroaryl, optionally substituted silyl, or optionally substituted sulfonyl;

R is hydrogen or optionally substituted alkyl; and t is 0, 1, 2, 3 ,4 ,5, 6, 7, 8, 9, or 10.

16. The compound of claim 1, wherein at least one $R^4$ is a metal.

17. The compound of claim 1, wherein $R^5$ is an electrophile.

18. The compound of claim 1, wherein n is an integer between 16 and 500.

* * * * *

UNITED STATES PATENT AND TRADEMARK OFFICE
CERTIFICATE OF CORRECTION

PATENT NO. : 11,155,527 B2  
APPLICATION NO. : 16/592199  
DATED : October 26, 2021  
INVENTOR(S) : Jeremiah A. Johnson et al.

Page 1 of 1

It is certified that error appears in the above-identified patent and that said Letters Patent is hereby corrected as shown below:

In the Claims

At Column 1, Claim 1, Line 44, please replace:
"$SR^{190}$"
With:
--SR#--

Signed and Sealed this
First Day of March, 2022

Drew Hirshfeld
*Performing the Functions and Duties of the
Under Secretary of Commerce for Intellectual Property and
Director of the United States Patent and Trademark Office*